(12) United States Patent
Tal et al.

(10) Patent No.: US 11,000,193 B2
(45) Date of Patent: May 11, 2021

(54) BLOOD PRESSURE MEASUREMENT SYSTEM USING FORCE RESISTIVE SENSOR ARRAY

(71) Applicant: LiveMetric (Medical) S.A., Luxembourg (LU)

(72) Inventors: Nir Efraim Joseph Tal, Haifa (IL); Adi Rabinovich, Netanya (IL); Tomer Bentzion, Tel Aviv (IL)

(73) Assignee: LiveMetric (Medical) S.A., Luxembourg (LU)

( * ) Notice: Subject to any disclaimer, the term of this patent is extended or adjusted under 35 U.S.C. 154(b) by 428 days.

(21) Appl. No.: 15/827,493

(22) Filed: Nov. 30, 2017

(65) Prior Publication Data

US 2018/0184923 A1    Jul. 5, 2018

Related U.S. Application Data

(60) Provisional application No. 62/442,189, filed on Jan. 4, 2017.

(51) Int. Cl.
*A61B 5/021* (2006.01)
*G01L 23/18* (2006.01)
(Continued)

(52) U.S. Cl.
CPC .......... *A61B 5/02141* (2013.01); *A61B 5/021* (2013.01); *A61B 5/681* (2013.01);
(Continued)

(58) Field of Classification Search
CPC ....... A61B 5/00; A61B 5/6892; A61B 5/1036; A61B 5/447; A61B 5/742;
(Continued)

(56) References Cited

U.S. PATENT DOCUMENTS 4,605,010 A    8/1986 Mcewen
5,243,992 A    9/1993 Eckerle et al.
(Continued)

FOREIGN PATENT DOCUMENTS

JP    357168183    10/1982
JP    2011239840    12/2011
(Continued)

OTHER PUBLICATIONS

Yousefi et al., "Adaptive Cancellation of Motion Artifacts in Waerable Biosensors", 34 Conf. IEEE EMBS, pp. 2004-2208, Aug. 28, 2012.
(Continued)

*Primary Examiner* — Eric J Messersmith
(74) *Attorney, Agent, or Firm* — The Roy Gross Law Firm, LLC; Roy Gross

(57) ABSTRACT

A novel and useful pressure sensor array incorporating sensor elements constructed from electrically conductive film as a substrate. Examples of commercially available electrically conductive (i.e. piezoresistive) film include Velostat and Linqstat. A wearable device is described incorporating an array of pressure sensors with flexible properties and a biocompatible material interface between the sensor elements and a user's skin. The pressure sensor array uses the electrically conductive film as a substrate and places a pair of conductors in a suitable configuration to form individual sensor elements. The sensor elements detect the change in resistance of the electrically conductive film when pressure is applied thereto. The sensor elements may be implemented in an interdigitated or opposing configuration. The sensor array also comprises a mechanical interface on top of the sensor elements for transferring or focusing the applied pressure to the electrically conductive film.

18 Claims, 10 Drawing Sheets

(51) Int. Cl.
- *G01L 9/06* (2006.01)
- *A61B 5/00* (2006.01)
- *A61B 5/024* (2006.01)
- *A61B 5/0402* (2006.01)
- *A61B 5/022* (2006.01)
- *A61B 5/145* (2006.01)
- *A61B 5/1455* (2006.01)

(52) U.S. Cl.
CPC .......... *A61B 5/742* (2013.01); *G01L 9/06* (2013.01); *G01L 23/18* (2013.01); *A61B 5/022* (2013.01); *A61B 5/024* (2013.01); *A61B 5/02416* (2013.01); *A61B 5/0402* (2013.01); *A61B 5/14532* (2013.01); *A61B 5/14551* (2013.01); *A61B 5/6824* (2013.01); *A61B 5/6831* (2013.01); *A61B 5/746* (2013.01); *A61B 5/7455* (2013.01); *A61B 2562/0247* (2013.01); *A61B 2562/043* (2013.01)

(58) Field of Classification Search
CPC ...... A61B 2562/0247; A61B 2562/046; A61B 2562/12; A61B 2562/164; A61B 5/021; A61B 5/022; A61B 5/023; G01L 1/18; A61G 7/0527; A61G 2203/34
See application file for complete search history.

(56) References Cited

U.S. PATENT DOCUMENTS

| | | | |
|---|---|---|---|
| 7,395,105 | B2 | 7/2008 | Schmidt et al. |
| 7,438,687 | B2 | 10/2008 | Lewicke |
| 7,539,532 | B2 | 5/2009 | Tran |
| 7,641,614 | B2 | 1/2010 | Asada et al. |
| 8,747,327 | B2 | 6/2014 | Kim et al. |
| 9,149,230 | B2 | 10/2015 | Caron et al. |
| 9,398,880 | B2 | 7/2016 | Barnett |
| 9,504,392 | B2 | 11/2016 | Caron et al. |
| 2003/0065269 | A1 | 4/2003 | Vetter et al. |
| 2006/0036185 | A1 | 2/2006 | Lewicke et al. |
| 2007/0055163 | A1 | 3/2007 | Asada et al. |
| 2007/0265533 | A1 | 11/2007 | Tran |
| 2008/0091113 | A1* | 4/2008 | Kondo ............... A61B 5/02241 600/485 |
| 2008/0228089 | A1 | 9/2008 | Cho et al. |
| 2009/0151475 | A1* | 6/2009 | Masaki ................ G01L 1/146 73/862.68 |
| 2010/0286538 | A1 | 11/2010 | Kim et al. |
| 2010/0298895 | A1 | 11/2010 | Ghaffari et al. |
| 2011/0112379 | A1 | 5/2011 | Li et al. |
| 2011/0152700 | A1 | 6/2011 | Sawanoi et al. |
| 2011/0166461 | A1 | 7/2011 | Susstrunk et al. |
| 2012/0053424 | A1 | 3/2012 | Kenalty et al. |
| 2014/0081160 | A1 | 3/2014 | Xiang |
| 2014/0180152 | A1 | 6/2014 | Maskara et al. |
| 2014/0243709 | A1* | 8/2014 | Gibson ............... A61B 5/6892 600/587 |
| 2014/0249386 | A1 | 9/2014 | Caron et al. |
| 2014/0288383 | A1 | 9/2014 | Barnett |
| 2014/0288443 | A1 | 9/2014 | Meriheina et al. |
| 2014/0288445 | A1 | 9/2014 | Makkonen et al. |
| 2014/0330145 | A1 | 11/2014 | Brodnick |
| 2014/0358012 | A1 | 12/2014 | Richards et al. |
| 2015/0366518 | A1 | 12/2015 | Sampson |
| 2015/0370398 | A1* | 12/2015 | Perlin ................. G06F 3/0414 345/173 |
| 2016/0066894 | A1 | 3/2016 | Barton-sweeney |
| 2016/0094899 | A1 | 3/2016 | Aumer et al. |
| 2016/0113517 | A1 | 4/2016 | Lee et al. |
| 2016/0262695 | A1 | 9/2016 | Zhang et al. |
| 2016/0278645 | A1 | 9/2016 | Yoon |
| 2016/0287110 | A1 | 10/2016 | Morris et al. |
| 2016/0367406 | A1 | 12/2016 | Barnett |
| 2017/0360306 | A1* | 12/2017 | Narasimhan ......... A61B 5/0053 |
| 2018/0325454 | A1* | 11/2018 | Petelenz ............. A61B 5/1038 |

FOREIGN PATENT DOCUMENTS

| | | |
|---|---|---|
| JP | 2015501184 | 1/2015 |
| JP | 5561674 B2 | 7/2017 |
| WO | WO 2005/094672 A1 | 10/2005 |
| WO | WO 2006/020956 A2 | 2/2006 |
| WO | WO 2006/094107 A1 | 9/2006 |
| WO | WO 2007/024777 A2 | 3/2007 |
| WO | WO 2009/125349 A2 | 10/2009 |
| WO | WO 2013/061281 A1 | 5/2013 |
| WO | WO 2014/153399 A1 | 9/2014 |
| WO | WO 2015/107269 A1 | 7/2015 |
| WO | WO 2015/143259 A1 | 9/2015 |
| WO | WO 2015/172897 A1 | 11/2015 |
| WO | WO 2015/183470 A9 | 12/2015 |
| WO | WO 2016/040253 A1 | 3/2016 |
| WO | WO 2016/040256 A1 | 3/2016 |
| WO | WO 2016/041073 A1 | 3/2016 |
| WO | WO 2016/061668 A1 | 4/2016 |
| WO | WO 2016/065463 A1 | 5/2016 |
| WO | WO 2016/065476 A1 | 5/2016 |
| WO | WO 2016/161227 A2 | 10/2016 |
| WO | WO 2017/074713 A1 | 5/2017 |
| WO | WO 2018/081208 A1 | 5/2018 |

OTHER PUBLICATIONS

Valle-Lopera et al., "Test and fabrication of piezoresistive sensors for contact pressure measurement", Revista Facultad de Ingeniería, Univ Antigua, No. 82, pp. 47-52, 2017.
International Search Report issued in PCT/US2016/056958 dated Jan. 26, 2017.
International Search Report issued in PCT/US2017/058197 dated Mar. 1, 2018.
International Search Report issued in PCT/US2017/058419 dated Apr. 12, 2018.
International Search Report issued in PCT/US2017/058420 dated Apr. 12, 2018.
Written Opinion issued in PCT/US2016/056958 dated Jan. 26, 2017.
Written Opinion issued in PCT/US2017/058197 dated Mar. 1, 2018.
Written Opinion issued in PCT/US2017/058419 dated Apr. 12, 2018.
Written Opinion issued in PCT/US2017/058420 dated Apr. 12, 2018.
Connell et al., "Continuous Wearable Blood Pressure Monitor", Medical Design Briefs, p. 22, Nov. 2016.
Aditya et al (2015) Novel Applications of Force Sensing Resistors in Healthcare Technologies, Proceedings of Healthy World Conference.
Aditya et al (2015) Real Time Monitoring of Arterial Pulse Waveform Parameters Using Low Cost, Non-invasive force transducer, Proceedings of Advancements in Medical Electronics.
Luo N, Dai W, Li C, et al. Flexible Piezoresistive Sensor Patch Enabling Ultralow Power Cuffless Blood Pressure Measurement, Advanced Functional Materials, 2016, 26(8):1178-1187.

* cited by examiner

BLOOD PRESSURE MEASUREMENT SYSTEM USING FORCE RESISTIVE SENSOR ARRAY

REFERENCE TO PRIORITY APPLICATION

This application claims the benefit of U.S. Provisional Application No. 62/442,189, filed Jan. 4, 2017, entitled "Blood Pressure Measurement System Using Force Resistive Sensor Array," incorporated herein by reference in its entirety.

FIELD OF THE DISCLOSURE

The subject matter disclosed herein relates to the field of monitoring vital signs of a user and more particularly relates to a system and method for blood pressure signal acquisition using a force resistive sensor array.

BACKGROUND OF THE INVENTION

High blood pressure is a common condition in which the long-term force of the blood against your artery walls is high enough that it may eventually cause health problems, such as heart disease. Blood pressure is determined both by the amount of blood your heart pumps and the amount of resistance to blood flow in your arteries. The more blood your heart pumps and the narrower your arteries, the higher your blood pressure.

One can have high blood pressure (i.e. hypertension) for years without any symptoms. Even without symptoms, damage to blood vessels and one's heart continues and can be detected. Uncontrolled high blood pressure increases one's risk of serious health problems, including heart attack and stroke. High blood pressure generally develops over many years, and it affects nearly everyone eventually. Fortunately, high blood pressure can be detected.

Currently, cardiovascular diseases represent a large proportion of all reported deaths globally. These diseases are considered a severe and shared risk, with a majority of the burden in low and middle-income countries. A major factor that increases the risk of heart failures or strokes, speeds up hardening of blood vessels and reduces life expectancy is hypertension or high blood pressure.

Hypertension is a chronic health condition in which the pressure exerted by the circulating blood upon the walls of blood vessels is elevated. In order to ensure appropriate circulation of blood in blood vessels, the heart of a hypertensive person must work harder than normal, which increases the risk of heart attack, stroke and cardiac failure. Eating a healthy diet and exercising, however, can significantly improve blood pressure control and decrease the risk of complications. Efficient drug treatments are also available. It is therefore important to find persons with elevated blood pressures and monitor their blood pressure information on a regular basis.

During each heartbeat, the blood pressure varies between a maximum (i.e. systolic) and a minimum (i.e. diastolic) pressure. A traditional noninvasive way to measure blood pressure has been to use a pressurized cuff and detect the pressure levels where the blood flow starts to pulsate (i.e. cuff pressure is between the systolic and diastolic pressure) and where there is no flow at all (i.e. cuff pressure exceeds systolic pressure). It has been seen, however, that users tend to consider the measurement situations, as well as the pressurized cuff tedious and even stressing, especially in long-term monitoring. In addition, the well-known white-coat syndrome tends to elevate the blood pressure during the measurement which leads to inaccurate diagnoses.

The use of wearable devices for monitoring body physiological parameters (e.g. blood pressure, heart rate (HR) pulse, body temperature, blood glucose level, movement patterns, etc.) non-invasively, continuously and/or intermittently for extended periods of time are becoming popular as a way to monitor and improve health.

Traditional blood pressure measurements require inflatable cuffs, which are gradually deflated from a state of full vessel occlusion to a lower pressure while listening using a mechanical sensor (e.g., stethoscope) to the sounds generated by the blood flow eddies in the vessel. An advantage of this method is its relative robustness to movements, while a disadvantage is its large form factor and the need for either manual inflation by the user or an automatic pump, which requires large quantities of energy. Since energy efficiency and small form factor are major requirements in wearable devices, inflatable cuff blood pressure sensing is not a useful paradigm in this space.

Prior art blood pressure measurement devices have significant disadvantages. First, the positioning or placement of the sensor on the radial artery is challenging to the user. Second, the sensor typically requires calibration in order to obtain correct readings. Third, the signal to noise ratio (SNR) obtained from the sensor might not be sufficient to obtain reliable blood pressure readings.

There is thus a need for a mechanism capable of continuously measuring and monitoring blood pressure that overcomes the disadvantages of traditional prior art devices and methods. For example, the mechanism of measuring blood pressure should not require the use of an inflatable cuff with its associated high energy requirements. In addition, the mechanism should be able to sense the blood pressure waveform on one or more of the arteries in the arm (i.e. the radial and ulnar arteries).

SUMMARY OF THE INVENTION

The present invention is a pressure sensor array incorporating sensor elements constructed from electrically conductive film as a substrate. Examples of commercially available electrically conductive (i.e. piezoresistive) film include Velostat and Linqstat. A wearable device is described incorporating an array of pressure sensors with flexible properties and a biocompatible material interface between the sensor elements and a user's skin. The pressure sensor array uses the electrically conductive film as a substrate and places a pair of conductors in a suitable configuration to form individual sensor elements. The sensor elements detect the change in resistance of the electrically conductive film when pressure is applied thereto.

The sensor elements may be implemented in an interdigitated or opposing configuration. The sensor array also comprises a mechanical interface on top of the sensor elements for transferring or focusing the applied pressure to the electrically conductive film. It is noted this solution is much cheaper, more flexible and has a more comfortable interface to the skin. Furthermore, the relative cost-effectiveness of this solution allows for a considerably higher number of sensor elements to be constructed alleviating problems such as placement and signal to noise ratio (SNR) that would otherwise be present when using only a handful of sensor elements.

There is thus provided in accordance with the invention, a sensor for blood pressure signal acquisition, comprising a substrate having a top surface and a bottom surface, the substrate incorporating a force resistive electrically conductive sensing film, a mechanical element coupled to the top surface of the sensing film, the mechanical element operative to transfer pressure from its top surface toward the sensing film when in contact with a user, and a pair of conductive elements affixed to one of the top or bottom surfaces of the sensing film, the pair of conductive elements spaced apart such that a change in resistance of the sensing film upon application of pressure to the mechanical element is capable of being detected.

There is also provided in accordance with the invention, a sensor for blood pressure signal acquisition, comprising a substrate having a top surface and a bottom surface, the substrate incorporating a force resistive electrically conductive sensing film, a first conductive element affixed to the top surface of the sensing film, a mechanical element coupled to the first conductive element, the mechanical element operative to transfer pressure from its top surface toward the sensing film when in contact with a user, a second conductive element affixed to the bottom surface of the sensing film, the first and second conductive elements spaced apart such that a change in resistance of the sensing film upon application of pressure to the mechanical element is capable of being detected.

There is further provided in accordance with the invention, a wearable device for measuring blood pressure of a user, comprising a housing, a display mounted in the housing, a wrist strap coupled to the housing, a processor coupled to a memory, at least one sensor array including a plurality of sensing elements coupled to a sensor circuit and operative to acquire a blood pressure signal, each sensing element comprising a substrate having a top surface and a bottom surface, the substrate incorporating a force resistive electrically conductive sensing film, a mechanical element coupled to the top surface of the sensing film, the mechanical element operative to transfer pressure from its top surface toward the sensing film when in contact with a user, and first and second conductive elements affixed to the sensing film, the first and second conductive elements spaced apart such that a change in resistance of the sensing film upon application of pressure to the mechanical element is capable of being detected.

BRIEF DESCRIPTION OF THE DRAWINGS

The present invention is explained in further detail in the following exemplary embodiments and with reference to the figures, where identical or similar elements may be partly indicated by the same or similar reference numerals, and the features of various exemplary embodiments being combinable. The invention is herein described, by way of example only, with reference to the accompanying drawings, wherein.

DETAILED DESCRIPTION

Figure 1:
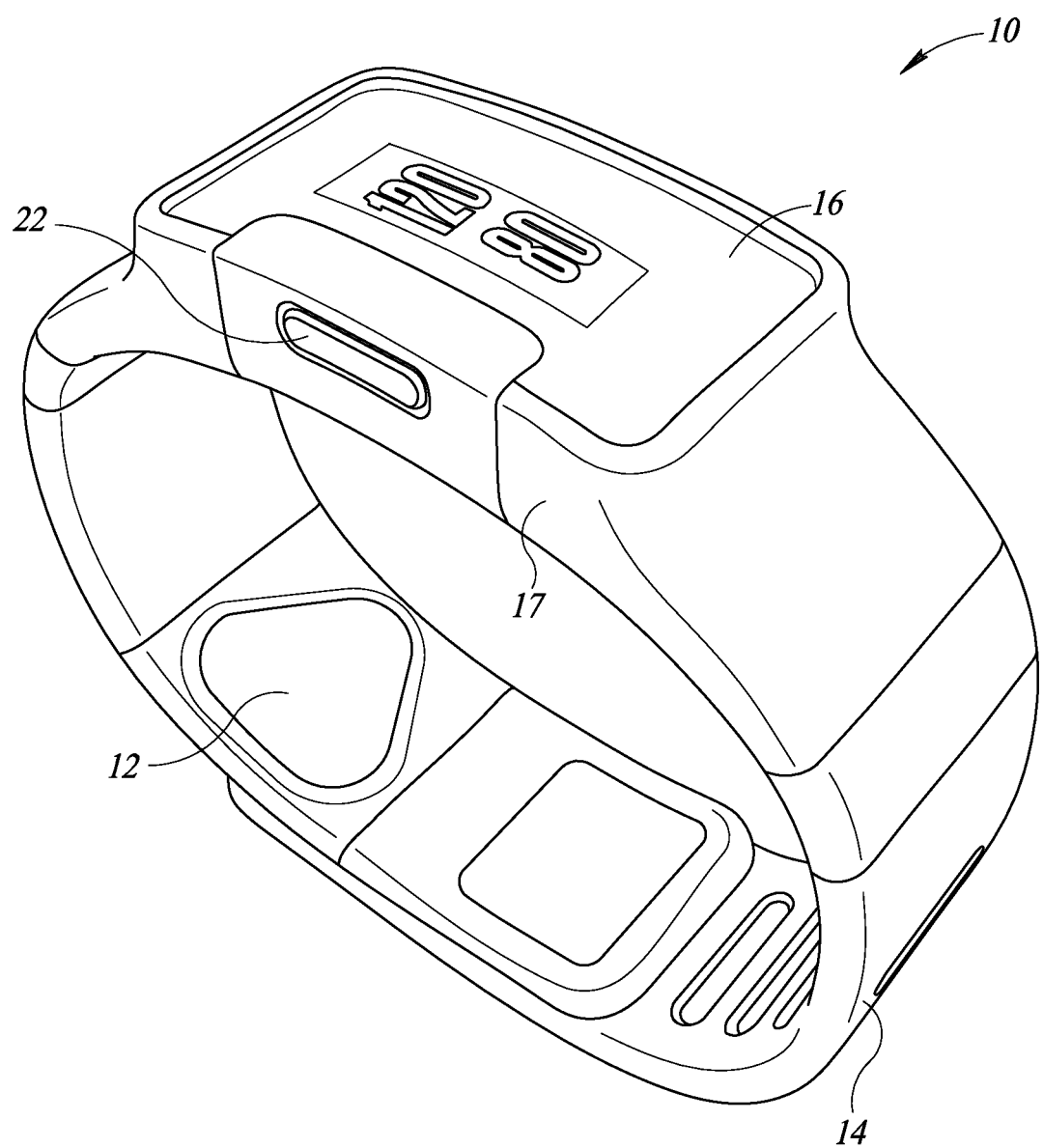
FIG. 1 is a diagram illustrating a first view of an example wearable device of the present invention operative to measure a user's blood pressure.

In the following detailed description, numerous specific details are set forth in order to provide a thorough understanding of the invention. It will be understood by those skilled in the art, however, that the present invention may be practiced without these specific details. In other instances, well-known methods, procedures, and components have not been described in detail so as not to obscure the present invention.

Among those benefits and improvements that have been disclosed, other objects and advantages of this invention will become apparent from the following description taken in conjunction with the accompanying figures. Detailed embodiments of the present invention are disclosed herein; however, it is to be understood that the disclosed embodiments are merely illustrative of the invention that may be embodied in various forms. In addition, each of the examples given in connection with the various embodiments of the invention which are intended to be illustrative, and not restrictive.

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings.

The figures constitute a part of this specification and include illustrative embodiments of the present invention and illustrate various objects and features thereof. Further, the figures are not necessarily to scale, some features may be exaggerated to show details of particular components. In addition, any measurements, specifications and the like shown in the figures are intended to be illustrative, and not restrictive. Therefore, specific structural and functional details disclosed herein are not to be interpreted as limiting, but merely as a representative basis for teaching one skilled in the art to variously employ the present invention. Further, where considered appropriate, reference numerals may be repeated among the figures to indicate corresponding or analogous elements.

Because the illustrated embodiments of the present invention may for the most part, be implemented using electronic components and circuits known to those skilled in the art, details will not be explained in any greater extent than that considered necessary, for the understanding and appreciation of the underlying concepts of the present invention and in order not to obfuscate or distract from the teachings of the present invention.

Any reference in the specification to a method should be applied mutatis mutandis to a system capable of executing the method. Any reference in the specification to a system should be applied mutatis mutandis to a method that may be executed by the system.

Throughout the specification and claims, the following terms take the meanings explicitly associated herein, unless the context clearly dictates otherwise. The phrases "in one embodiment," "in an example embodiment," and "in some embodiments" as used herein do not necessarily refer to the same embodiment(s), though it may. Furthermore, the phrases "in another embodiment," "in an alternative embodiment," and "in some other embodiments" as used herein do not necessarily refer to a different embodiment, although it may. Thus, as described below, various embodiments of the invention may be readily combined, without departing from the scope or spirit of the invention.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" include plural references. The meaning of "in" includes "in" and "on."

Figure 2:
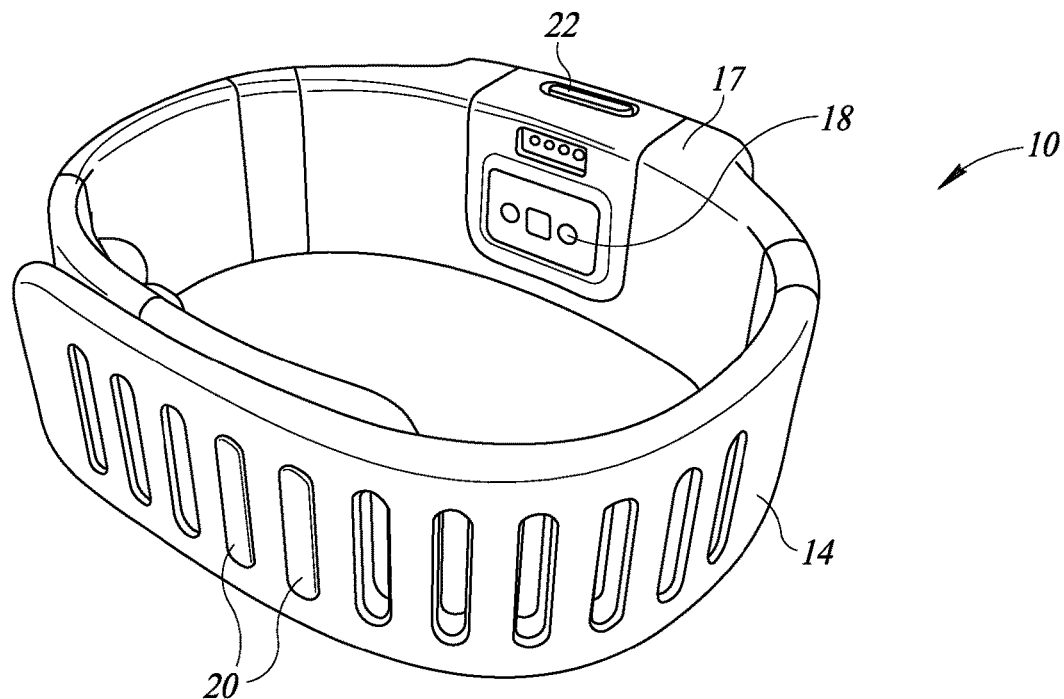
FIG. 2 is a diagram illustrating a second view of an example wearable device of the present invention operative to measure a user's blood pressure.

A diagram illustrating a first view of an example wearable device of the present invention operative to measure a user's blood pressure from the radial and/or the ulnar artery is shown in FIG. 1. A diagram illustrating a second view of an example wearable device of the present invention operative to measure a user's blood pressure is shown in FIG. 2. A diagram illustrating pressure sensors incorporated within a wearable device and configured to sense pressure from the radial and/or the ulnar artery is shown in FIG. 3.

Figure 3:
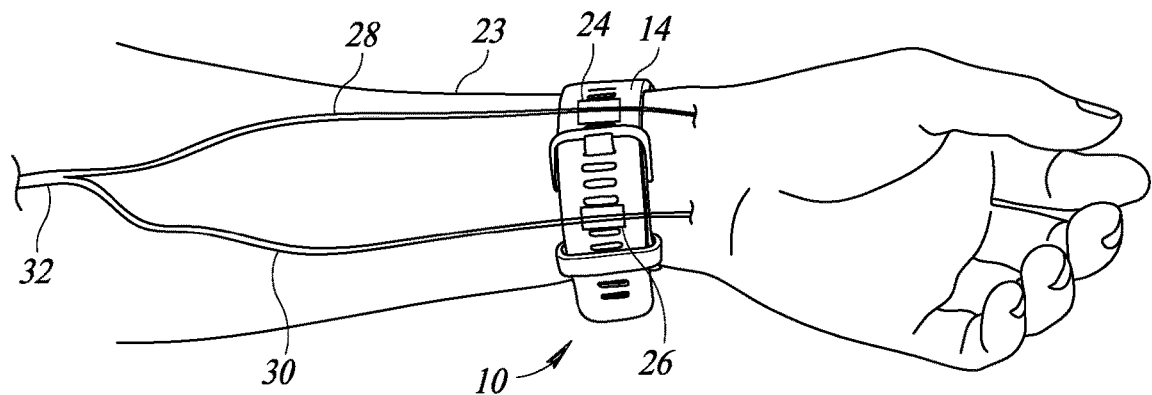
FIG. 3 is a diagram illustrating pressure sensors incorporated within a wearable device and configured to sense pressure from the radial and/or the ulnar artery.

With reference to FIGS. 1, 2, and 3, the wearable device, generally referenced 10, comprises a display 16 (e.g., viewable OLED, etc.) mounted in a housing 17 containing a CPU, memory, wired and wireless communications, etc., one or more buttons, switches or dials 22, wrist band (straps) 14 housing a pressure sensor array 12 that includes one or more pressure sensors 24, 26 adapted to sense pressure of the radial 28 and/or ulnar 30 arteries, one or more optical or other non-pressure sensors 18, and strap closure, clasp, holding, fastening or lock mechanism 20. The wrist band strap has an embedded pressure sensor on it and is intended to be closed against the wrist whilst applying sensor array 12 on at least one of the radial, ulnar and brachial arteries and apply medium pressure thereon (i.e. significantly less than the systolic pressure but enough to sense the pressure wave).

In one example, the wearable consumer product device 10 is a wearable multifunctional electronic device including multiple functionalities such as time keeping, health monitoring, sports monitoring, medical monitoring, communications to a host device and/or a cloud server, navigation, computing operations, and/or the like. The functionalities may include but are not limited to: keeping time; monitoring a user's physiological signals (e.g., heart rate, blood pressure, etc.) and providing health-related information based on those signals; communicating (in a wired or wireless fashion) with other electronic devices or services, which may be different types of devices having different functionalities; providing alerts to a user, which may include audio, haptic, visual and/or other sensory output, any or all of which may be synchronized with one another; visually depicting data on a display; gathering data form one or more sensors that may be used to initiate, control, or modify operations of the device; determining a location of a touch on a surface of the device and/or an amount of force exerted on the device, and using either or both as input; accepting voice input to control one or more functions; accepting tactile input to control one or more functions; capturing and transmitting images; and so on.

The device 10 can take a variety of forms. In one example, the device is a wrist worn electronic device. The device may include a variety of types of form factors including, wristbands, armbands, bracelets, jewelry, and/or the like.

A wearable consumer product is one that can be worn by or otherwise secured to a user. Note that a wearable consumer product can be worn by a user in a variety of ways such as around the wrist. In this case, the device includes a band or wrist strap that can be wrapped around a user's wrist to secure the device to the user's body. The device may include one or more other types of attachments including, for example, an armband, lanyard, waistband, chest strap, etc.

In one embodiment, the device comprises a housing 17 that carries, encloses and supports both externally and internally various components (including, for example, integrated circuit chips and other circuitry) to provide computing and functional operations for the device. The components may be disposed on the outside of the housing, partially within the housing, through the housing, completely inside the housing, and the like. The housing may, for example, include a cavity for retaining components internally, holes or windows for providing access to internal components, and various features for attaching other components. The housing may also be configured to form a water resistant or waterproof enclosure. For example, the housing may be formed from as a single unitary body and the openings in the unitary body may be configured to cooperate with other components to form a water-resistant or waterproof barrier. In another embodiment, the housing may not comprise a cavity but rather is constructed from plastic where the device electronics are molded into the plastic.

Examples of components that may be contained in the device include processing units, memory, display, sensors, biosensors, speakers, microphones, haptic actuators, accelerometers, gyroscopes, batteries, and so on. In some cases, the device may take on a small form factor. In cases such as these, the components may be packaged and/or in order to provide the most functionality in the smallest space. The components may also be configured to take up a minimal amount of space, which may facilitate the device having a small form factor. Additionally, the integration and assembly of the various components may be configured to enhance the reliability of the device.

The construction of the housing may be widely varied. For example, housing may be formed from a variety of materials including plastic, rubber, wood, silicone, glass, ceramics, fiber composites, metal or metal alloys, (e.g., stainless steel, aluminum), precious metals (e.g., gold, silver), or other suitable materials, or a combination of these materials.

Also in the illustrated embodiment, the wearable electronic device includes a band 14 or strap or other means for attaching to a user's arm 23. The band may, for example, be configured to attach to the body and provide a loop for securing to the wrist of the user. The band may be integral with the housing or it may be a separate part. If integral, the band can be a continuation of the housing. In some cases, the integral band may be formed from the same material as the housing. If the band is separate, the band may be fixed or releasably coupled to the housing. In both cases, the band may be formed from similar or different materials as the housing. In most cases, the band is formed from a flexible material such as an elastomer such that it can conform to a user's body. Furthermore, the band itself may be a single integral part or it may include attachment ends that provide an open and closed configuration. The attachment ends may, for example, be manifested as a clasp or other similar attachment mechanism or device. This particular configuration allows a user to open the band for placement on the arm and close the band in order to secure the band and body to the arm. The band may be widely varied. By way of example, they may be formed from rubber, silicone, leather, metal, mesh, links and/or the like.

Figure 4:
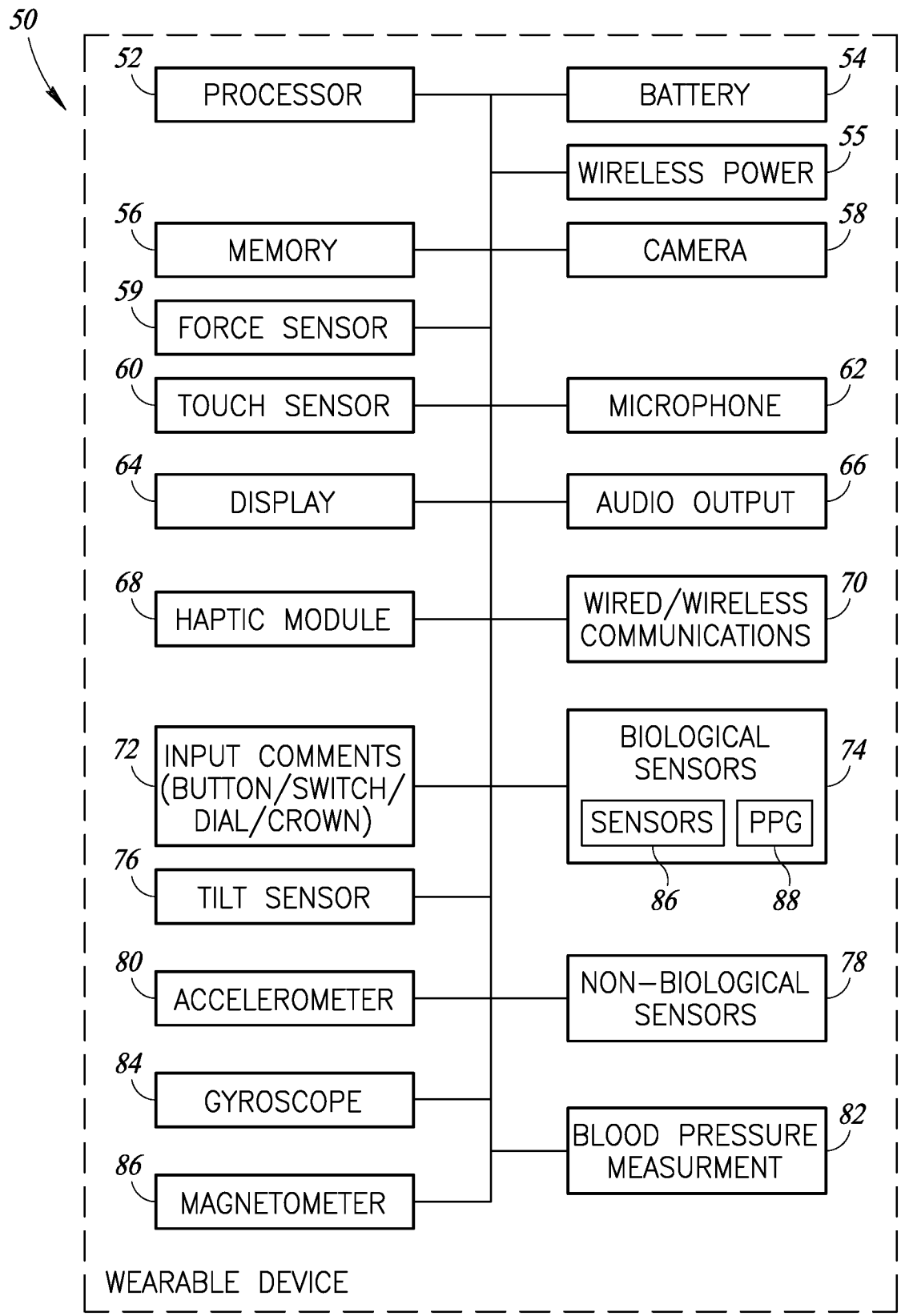
FIG. 4 is a high-level block diagram illustrating an example wearable electronic device incorporating the blood pressure measurement mechanism of the present invention.

A high-level block diagram illustrating an example wearable electronic device incorporating the blood pressure measurement mechanism of the present invention is shown in FIG. 4. By way of example, device 50 may correspond to the consumer product 10 shown in FIGS. 1, 2, and 3 described supra. To the extent that multiple functionalities, operations, and structures are disclosed as being part of, incorporated into, or performed by device 50, it should be understood that various embodiments may omit any or all such described functionalities, operations, and structures. Thus, different embodiments of the device 50 may have some, none, or all of the various capabilities, apparatuses, physical features, modes, and operating parameters discussed herein.

The device 50 comprises one or more processing units 52 that are configured to access a memory 56 having instructions stored thereon. The instructions or computer programs may be configured to perform one or more of the operations or functions described with respect to the device 50. For example, the instructions may be configured to control or coordinate the operation of a display 64, one or more input/output components such as the touch sensor 60, etc., one or more communication channels 70, one or more sensors such as biological sensors 74 and non-biological sensors 78, a speaker 66, a microphone 62, and/or one or more haptic feedback devices 68.

The processing units 52 may be implemented as any electronic device capable of processing, receiving, or transmitting data or instructions. For example, the processing units may include one or more of: a microprocessor, a central processing unit (CPU), an application-specific integrated circuit (ASIC), a digital signal processor (DSP), or combinations of such devices. As described herein, the term "processor" is meant to encompass a single processor or processing unit, multiple processors, multiple processing units, or other suitably configured computing element or elements.

For example, the processor may comprise one or more general purpose CPU cores and optionally one or more special purpose cores (e.g., DSP core, floating point, etc.). The one or more general purpose cores execute general purpose opcodes while the special purpose cores execute functions specific to their purpose.

The memory 56 comprises dynamic random access memory (DRAM) or extended data out (EDO) memory, or other types of memory such as ROM, static RAM, flash, and non-volatile static random access memory (NVSRAM), removable memory, bubble memory, etc., or combinations of any of the above The memory stores electronic data that can be used by the device. For example, a memory can store electrical data or content such as, for example, audio and video files, documents and applications, device settings and user preferences, timing and control signals or data for the various modules, data structures or databases, and so on. The memory can be configured as any type of memory.

The display 64 functions to present visual or graphical output to a user. In some embodiments, the display includes a graphical user interface produced using an operating system or software application executed on one or more processing units of the device. In one example, the display includes a graphical depiction that resembles a watch face or other timekeeping device. In other examples, the display includes a graphical interface for an e-mail, text messaging, or other communication-oriented program. The display may also present visual information that corresponds to one of the other functional aspects of the device 50. For example, the display may include information that corresponds to the input of the biosensor 74, non-biosensor 78, force sensor 59, touch sensor 60, and others.

Input components 72 may include buttons, switches, dials, and crowns for accepting user input, and so on. Generally, the input components are configured to translate a user provided input into a signal or instructions that may be accessed using instructions executed on the processor. In the present example, the input components may include the hardware configured to receive the user input (e.g., button, switch, crown, and encoder) which is operatively coupled to circuitry and firmware used to generate signals or data that are able to be accessed using processor instructions. Each input component may include specialized circuitry for generating signals or data and, additionally or alternatively, circuitry and firmware for generating signals or data may be shared between multiple input components. In some cases, the input components produce user provided feedback for application specific input that corresponds to a prompt or user interface object presented on display 64. For example, a crown may be used to receive rotational input from the user, which may be translated into an instruction to scroll a list or object presented on the display. The input components may also produce user input for system level operations. For example, the input components may be configured to interact directly with hardware or firmware being executed on the device for system level operations, including, without limitation, power on, power off, sleep, awake, and do-not-disturb operations.

The device 50 may also comprise one or more acoustic elements, including audio outputs 66 (e.g., speaker, headphone jack, etc.) and a microphone 62. The audio output 66 may include drive electronics or circuitry and may be configured to produce an audible sound or acoustic signal in response to a command or input. Similarly, the microphone may also include drive electronics or circuitry and is configured to receive an audible sound or acoustic signal in response to a command or input. The speaker and the microphone may be acoustically coupled to respective ports or openings in the housing that allow acoustic energy to pass, but may prevent the ingress of liquid and other debris.

The speaker and microphone are also operatively coupled to the processor, which may control the operation of the speaker and microphone. In some cases, the processor is configured to operate the speaker to produce an acoustic output that corresponds to an application or system-level operation being performed on the device 50. In some cases, the speaker is operatively coupled to other modules, including, for example, input components 72, such as a crown or button. In some implementations, the device is configured to produce an audible output that corresponds to the operation of the crown or buttons using the speaker. The microphone may be configured to produce an output or signal in response to an acoustic stimulus. For example, the microphone may be operatively coupled to the memory 56 and may be configured to record audio input, including human speech, music, or other sounds. In some cases, the microphone may be configured to receive voice signals, which may be interpreted as voice commands by the processor.

Figure 5:
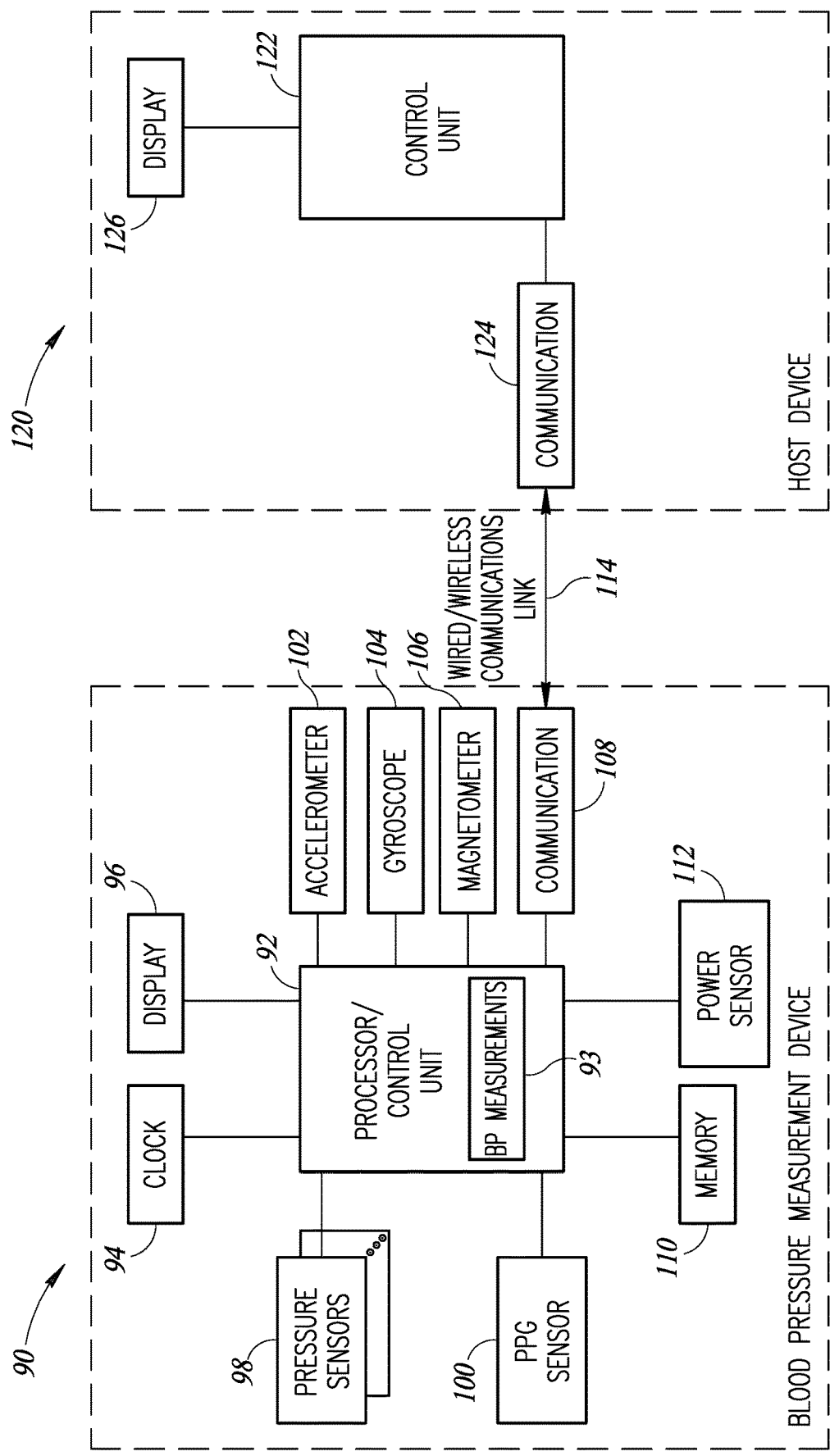
FIG. 5 is a high-level block diagram illustrating an example blood pressure measurement device such as a wearable in communication with an optional host device.

The one or more communication channels 70 may include one or more wired and/or wireless interface(s) that are adapted to provide communication between the processor 52 and an external device such as a host device 120 (FIG. 5). In general, the one or more communication channels may be configured to transmit and receive data and/or signals that may be interpreted by instructions executed on the processor. In some cases, the external device is part of an external communication network that is configured to exchange data with wireless devices. Generally, the wireless interface may include, without limitation, radio frequency, optical, acoustic, and/or magnetic signals and may be configured to operate over a wireless interface or protocol. Example wireless interfaces include radio frequency cellular interfaces, fiber optic interfaces, acoustic interfaces, Bluetooth interfaces (e.g., Bluetooth, Bluetooth Low Energy, etc.), infrared interfaces, USB interfaces, Wi-Fi interfaces, TCP/IP interfaces, network communications interfaces, or any conventional communication interfaces.

In some implementations, the one or more communications channels may include a dedicated wireless communication channel between the device and another user device, such as a mobile phone, tablet, computer, host device, or the like. In some cases, output, including audio sounds or visual display elements, are transmitted directly to the other user device for output to the user. For example, an audible alert or visual warning may be transmitted to a user's mobile phone for output on that device. Similarly, the one or more communications channels may be configured to receive user input provided on another user device. In one example, the user may control one or more operations on the device using a user interface on an external mobile phone, table, computer, or the like.

Additionally, the communications channels 70 may include a near field communication (NFC) interface. The NFC interface may be used to identify the device and initiate a secure data connection, which may be used to authorize transactions, purchases, or conduct other forms of e-commerce.

The device 50 also comprises one or more biological 74 and non-biological 78 sensors. Non-biological sensors 78 may include one or more different sensors, including devices and components that are configured to detect environmental conditions and/or other aspects of the operating environment. Examples include an ambient light sensor (ALS), proximity sensor, temperature sensor, barometric pressure sensor, moisture sensor, and the like. Thus, the non-biological 78 sensors may also be used to compute an ambient temperature, air pressure, and/or water ingress into the device. In some embodiments, non-biological 78 sensors may include one or more motion sensors for detecting movement and acceleration of the device. The one or more motion sensors may include one or more of the following: a tile sensor 76, accelerometer 80, gyroscope 84, magnetometer 86 or other type of inertial measurement device.

Motion sensor data can be used to monitor and detect changes in motion of the device. Changes in linear and angular motion may be used to determine or estimate an orientation of the device relative to a known location or fixed datum. The sensor input produced from the one or more motion sensors may also be used to track the movement of the user. The movement of the user may be used to facilitate navigation or map-guided functionality of the device. Additionally, input related to the gross movement of the user can be used as a pedometer or activity meter, which may be stored and tracked over time to determine health metrics or other health related information. Additionally, in some embodiments, sensor input from the one or more motion sensors may be used to identify motion gestures. For example, the motion sensors can be used to detect an arm raise or the position of a user's body (within a predetermined confidence level of certainty).

The device 50 also comprises one or more biological sensors (biosensors) 74 that may include optical and/or electronic biometric sensors that may be used to compute one or more health metrics. One or more of the biosensors may include one or more pressure sensors 86 for measuring blood pressure, a light source and a photodetector to form a photoplethysmography (PPG) sensor 88. The optical (e.g., PPG) sensor or sensors may be used to compute various health metrics including, without limitation, heart rate, a respiration rate, blood oxygenation level, blood volume estimate, blood pressure, or a combination thereof. One or more of the biosensors may also be configured to perform an electrical measurement using one or more electrodes in contact with the user's body. The electrical sensor(s) may be used to measure electrocardiographic (ECG) characteristics, galvanic skin resistance, and other electrical properties of the user's body. Additionally, or alternatively, one or more of the biosensors may be configured to measure body temperature, exposure to UV radiation, and other health related information.

The device 50 may also comprise one or more haptic devices 68. The haptic device may include one or more of a variety of haptic technologies such as, but not necessarily limited to, rotational haptic devices, linear actuators, piezoelectric devices, vibration elements, and so on. In general, the haptic device may be configured to provide punctuated and distinct feedback to a user of the device. More particularly, the haptic device may be adapted to produce a knock or tap sensation and/or a vibration sensation. The haptic device may be operatively coupled to the processor 52 and memory 56. In some embodiments, the haptic device may be directly controlled by the processor. In some embodiments, the haptic device may be controlled, at least in part, by the operation of an input component 72, including, for example, a button, dial, crown, or the like. The operation of the haptic device may also be paired or linked to the operation of one or more other output devices, including, for example, the display 64 or audio output device 66, e.g., a speaker. In one embodiment, haptic output may be produced using one or more electromechanical subassemblies that are configured to induce motion or vibration in the device, which may be perceived or sensed by the user.

The device 50 may comprise a battery or other suitable power source 54 that is used to store and provide power to the other components of the device. The battery may be a rechargeable power supply that is configured to provide power to the device while it is being worn by the user. The device may also be configured to recharge the battery using a wireless charging system. Accordingly, in some cases, the device may include a wireless power module 55 that may be configured to receive power from an external device or dock. The wireless power module may be configured to deliver power to components of the device, including the battery.

In some implementations, the device includes one or more receiving inductive coils that are configured to cooperate with one or more transmitting inductive coils that are located in a charging dock or other external device. The wireless charging system allows the transfer of power and/or wireless communications with the device without the use of an external port or terminal connection.

The wireless power module and an external charging station or dock may also be configured to transmit data between the device and a base or host device. In some cases, the wireless power module may interface with the wireless charging station or dock to provide an authentication routine that is able to identify specific hardware, firmware, or software on the device in order to facilitate device maintenance or product updates.

The device 50 may also comprise a variety of other components, including for example, a camera or camera modules 58. The camera may be configured to capture an image of a scene or subject located within a field of view of the camera. The image may be stored in a digital file in accordance with any one of a number of digital formats. In some embodiments, the device includes a camera, which includes an image sensor formed from a charge-coupled device (CCD) and/or a complementary metal-oxide-semiconductor (CMOS) device. The camera may also include one or more optical components disposed relative to the image sensor, including, for example, a lens, a filter, a shutter, and so on.

The device 50 may comprise a force sensor 59 configured to detect and measure the magnitude of a force of a touch on a surface of the device. The output of the force sensor can be used to control various aspects of the device. For example, the force sensor may be used to control an aspect, such as a cursor or item selection on a user interface presented on the display of the device. The force sensor may also be used to control the audio output, haptic output, and other functionality of the device. The force sensor may also be used to distinguish between different types of input from the user. For example, a light touch from the user may be interpreted as a scroll command and used to index or scroll through a list of items on the display. A harder touch from the user may be interpreted as a selection or confirmation of an item on the display.

The device 50 also may comprise a touch sensor 60 configured to detect and measure the location of a touch on a surface of the device. In some implementations, the touch sensor is a capacitive based touch sensor that is disposed relative to the display or display stack of the device. The touch sensor may be a separate nonintegrated sensor relative to the force sensor. In alternative embodiments, the touch sensor may also be physically and/or logically integrated with the force sensor to produce a combined output. The touch sensor may be used to control various aspects of the device, e.g., to control an aspect of the user interface presented on the display of the device, the audio output, haptic output, and other functionality of the device.

In some cases, the logical integration of the force sensor 59 and touch sensor 60 enhances the versatility or adaptability of device 50 by enabling a sophisticated user interface. For example, they may be combined to interpret a wider range of gestures and input commands than may be possible using, for example, only a touch input. For example, the force sensor may provide a magnitude of a force of a touch, which may be used to distinguish between two touch input commands that have a similar location or gesture path. An improved touch interface using both force sensor and touch sensor may be particularly advantageous when interpreting touch commands on a relatively small area surface, such as a display screen or cover glass of a wearable electronic device.

A high-level block diagram illustrating an example blood pressure measurement device such as a wearable in communication with an optional host device is shown in FIG. 5. The blood pressure measurement device, generally referenced 90, comprises a control unit/processor 92 incorporating, inter alia, blood pressure measurement processing block 93, clock source 94 such as a crystal oscillator, display 96, communications module 108, memory 110, power source 112, one or more pressure sensors 98, PPG sensor 100, and one or more motions sensors such as 3D Microelectromechanical system (MEMS) accelerometer 102, gyroscope 104 and/or magnetometer 106. The host device, generally referenced 120, comprises a control unit or processor 122, display 126 and communications module 124. Note that the device 90 may be incorporated into a wearable device such as shown in FIG. 4 described in detail supra.

Note that the one or more pressure sensors may comprise (1) a microelectromechanical system (MEMS) capacitive pressure sensor; (2) a patch sensor applied to the brachial artery; (3) an array of pressure sensors simultaneously collecting pressure data; (4) a pressure sensor array operative to generate a single pressure measurement; (5) a pressure sensor array operative to generate a plurality of pressure measurements; and (6) a pressure sensor array time domain multiplexed based on each sensor's respective signal quality.

In operation, the control unit is configured to receive data from multiple sources, process it and output waveforms, measurements and telematics. The one or more pressures sensors are adapted to sense pressure when pressed against a hand artery such as the radial, ulnar or brachial artery. The display is adapted to display waveforms, measurements (e.g., blood pressure, heart rate, temperature, etc.) and telematics such as battery status. The power source is adapted to provide energy for the various circuits and may comprise a battery (e.g., lithium ion or lithium ion polymer rechargeable battery). The memory function to store program and data. The device 90 may also comprise a photoplethysmography (PPG) sensor for independent measurement and synchronization of heart rate. The communication module functions to send data over a communication link 114 which may comprise a wired or wireless link. In one embodiment, the device transmits data when the link is available either continuously or intermittently, while in other times the device stores the data in volatile or non-volatile (NV) memory.

In one embodiment, the blood pressure measurement device 90 may be connected to the host unit 120. The host device is configured to communicate with the blood pressure measurement device over the link 114 using communication module 124. The control unit 122 is programmed to display information from or relating to measurements obtained (and optionally processed) by blood pressure measurement device 90.

The wearable device of the present invention provides an array of pressure sensors with flexible properties and a biocompatible material interface between the sensors and a user's skin. In one embodiment, the pressure sensor array uses a (i.e. electrically conductive) material such as Velostat or Linqstat electrically conductive film as a substrate and places conductors in a suitable configuration, e.g., in an interdigitated or opposing configuration to form multiple individual sensor elements. A characteristic of the Velostat and Linqstat electrically conductive material is that its resistance is reduced when pressure is applied to it. The array also comprises a mechanical interface placed over the sensor elements to create the sensor array. It is noted this solution is much cheaper, more flexible and has a more comfortable interface to the skin.

It is noted that Velostat and Linqstat are commercially available packaging materials made of a polymeric foil (polyolefines) impregnated with carbon black to make the material electrically conductive. Velostat (formerly a 3M product) is available from Desco Industries Inc., One Colgate Way, Canton, Mass. 02021, United States. Linqstat is available from Caplinq Corporation, 957 Snowshoe Crescent-Orleans, Ottawa ON, K1C 2Y3, Canada.

An advantage of the invention is that it provides a cost effective and non-invasive continuous blood pressure measurement device. By using off the shelf, inexpensive technology, such as piezoresistive electrically conductive film sheets, the need for complex MEMS devices is avoided while gaining the advantage of physical flexibility and a comfortable skin interface.

Figure 6:
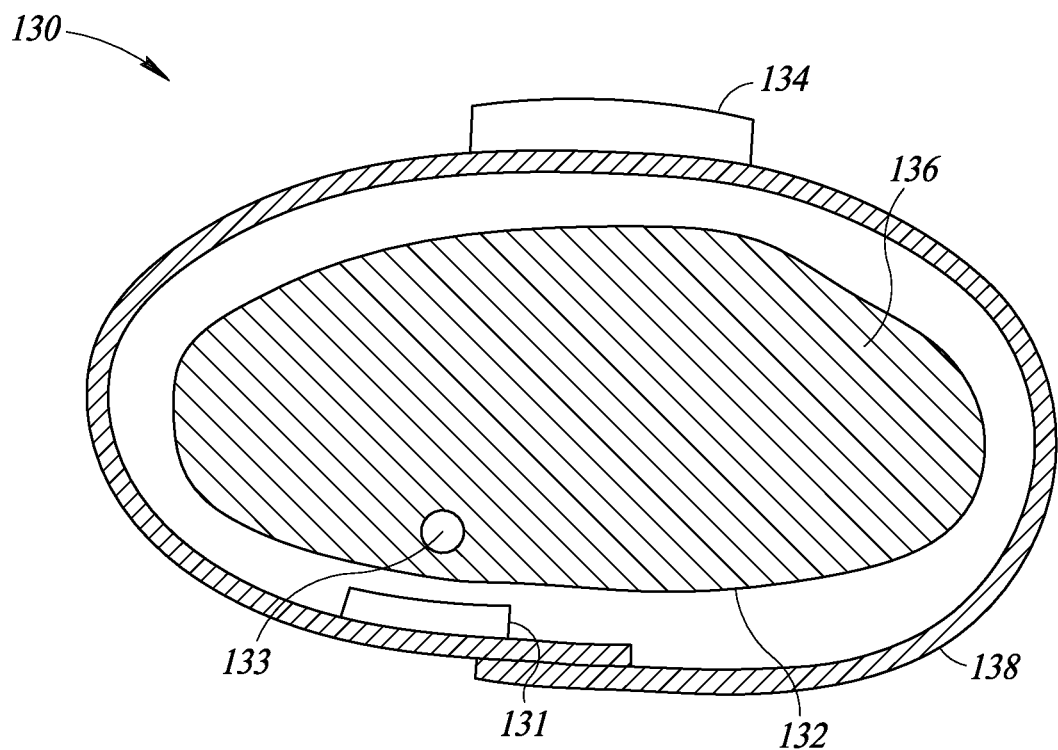
FIG. 6 is a diagram illustrating a side view of a wrist band in accordance with an embodiment of the present invention.

A diagram illustrating a side view of a wrist band in accordance with an embodiment of the present invention is shown in FIG. 6. The device, generally referenced 130, comprises a housing and display 134, wrist band 138, and pressure sensor array 131. Wrist strap 138 is configured to be closed around the skin surface 132 of a tubular extremity organ 136 (e.g., finger, wrist, arm, or leg) containing a target blood vessel 133 (e.g., brachial, radial, ulna, femoral, one of the palmar digital arteries, etc.) while applying moderate pressure (i.e. significantly less than the systolic pressure in blood vessel 142 but enough to sense the pressure wave).

The pressure sensor array 131 may comprise several different embodiments. Four example embodiments are shown in FIGS. 7, 8, 9, and 10 described in more detail infra with reference to FIG. 6.

Figure 7:
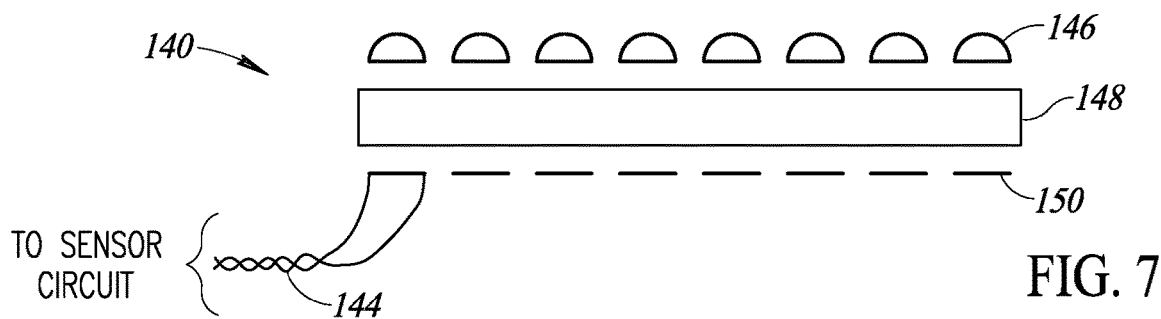
FIG. 7 is a diagram illustrating a first example pressure sensor array suitable for use with the present invention.

A diagram illustrating a first example pressure sensor array for use with the present invention is shown in FIG. 7. The pressure sensor array, generally referenced 140, is configured to be in contact with the organ 136 (FIG. 6) when the wearable device 10 (FIG. 1) is properly fastened to the user. The gap between the wrist band 138 (FIG. 6), sensor array 140 and the organ 136 is shown for clarity sake only, and normally would be minimal or not exist with a much tighter fit.

In one embodiment, the sensor 140 comprises force resistive sensing film or sheet 148 that is mounted on wrist strap 138 and constructed from piezoresistive electrically conductive materials such as Velostat or Linqstat. Both of these materials are made from polymeric foil impregnated with carbon black, that make them electrically conductive. When pressure is applied to these materials their resistance decreases. To sense pressure from the skin surface 132 and blood vessel 133, an array of interdigitated pairs of conductors (referred to as "sensing elements" or "sensing element array") 150 is fabricated on sheet 148 either on the top or bottom surface, using any suitable well-known process such as flexible printed circuit board (PCB) technology, such that the sensing elements 150 are printed on and touch sheet 148. Each conductor has a pair of wires 144 coming from each sensor within the array 150. For each element in the sensor array 150 there is a corresponding mechanical protruding element 146, which functions to transfer or direct (i.e. focus) pressure from the surface above and in contact with it towards a sensing element in sensing element array 150. Such elements may be constructed from either a hard material (e.g., resins, plastics, cement, etc.), or from softer materials, such as gel polymers (e.g., polydimethylsiloxane (PDMS), various other "silicones", etc.), or a combination thereof.

When wrist strap 138 is closed snug around the organ 136 moderate pressure is applied to the skin surface 132 and the mechanical protruding elements 146 are coupled with the skin 132. It is preferable that the protruding elements lie substantially over the sensing elements whether they are located on the top or bottom surface of the piezoresistive sheet. When the blood pressure mechanical wave advances through blood vessel 142, it couples through one or more of mechanical protruding elements 146 into one or more of the sensing elements 150 through piezoresistive sheet 148. The sheet area, through which the mechanical pressure wave experiences strain, undergoes a decrease in its resistance. This is picked up by one or more elements 150 in the sensor array and is transmitted via the wires 144 to the sensor circuit (not shown). The function of the sensor circuit is to convert the sensor signals, through digital data processing by a processor, into a blood pressure measurement.

Figure 8:
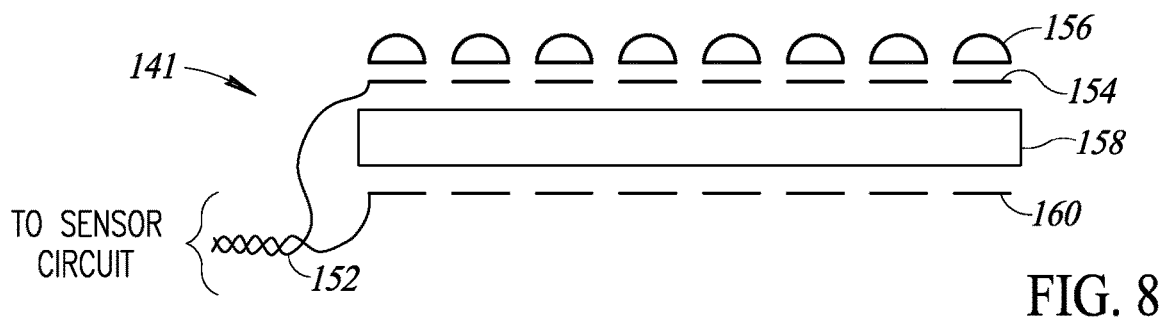
FIG. 8 is a diagram illustrating a second example pressure sensor array suitable for use with the present invention.

A diagram illustrating a second example pressure sensor array suitable for use with the present invention is shown in FIG. 8. The pressure sensor array, generally referenced 141, is configured to be in contact with the organ 136 (FIG. 6) when the wearable device 10 (FIG. 1) is properly fastened to the user. In one embodiment, force resistive sensing sheet (i.e. electrically conductive sheet) 158 is mounted on wrist strap 138 and constructed from piezoresistive materials such as Velostat or Linqstat. To sense pressure from the skin surface 132 and blood vessel 133, two opposing arrays of conductors 160 and 154 (referred to as "sensing elements" or "sensing element array") are fabricated on both sides of sheet 158 using any suitable well-known process such as flexible printed circuit board (PCB) technology, such that the conductive pairs 160, 154 touch sheet 158. The shape of each conductor is not critical as long as the desired force/resistance relationship is achieved for the particular implementation. Preferably, solid (i.e. contiguous) elements are used on both sides of the sensing sheet. An example of round (button) shaped conductors is shown in FIG. 11B described infra. Note that typically, interdigitated conductive fingers are not used due to the desire to attain as much force dependent resistance from the sensing sheet. Each conductor pair has a pair of wires 152 connected to it. For each conductor pair in 160, 154 there is a corresponding mechanical protruding element 156 which functions to direct pressure from the surface above it towards a sensing element in the sensing element array. Such elements may be constructed from either a hard material (resins, plastics, cement, etc.), or from softer materials such as gel polymers (e.g., polydimethylsiloxane (PDMS), various other "silicones", etc.), or a combination thereof.

When wrist strap 138 is closed snug around the organ 136 moderate pressure is applied to the skin surface 132 and the mechanical protruding elements 156 are coupled with the skin 132. When the blood pressure mechanical wave advances through blood vessel 133, it couples through one or more of mechanical protruding elements 156 into one or more of the sensing element conductive pairs 154 and 160 through piezoresistive sheet 158. The sheet area, through which the mechanical pressure wave experiences strain, undergoes a decrease in its resistance. This is picked up by one or more elements in sensor array conductive pairs 160 and 154, and is transmitted via the wires 152 to the sensor circuit (not shown). The function of the sensor circuit is to convert the sensor signals, through digital data processing by a processor, into a blood pressure measurement.

Figure 9:
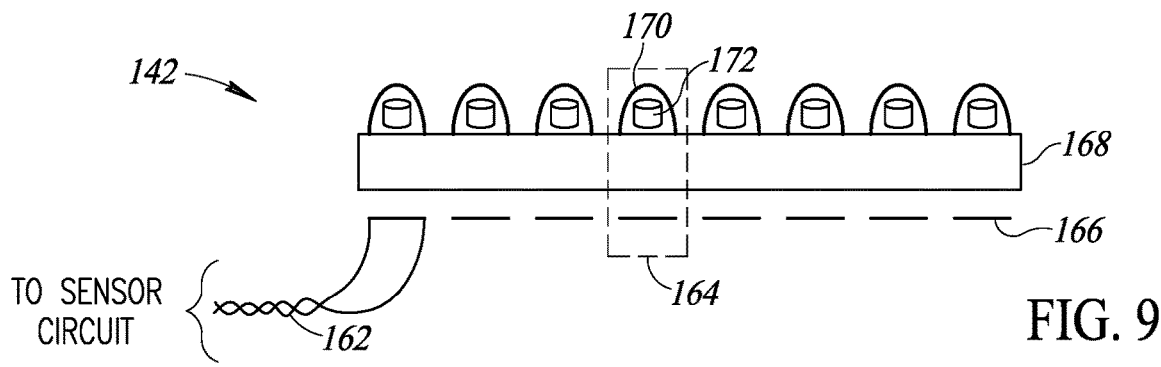
FIG. 9 is a diagram illustrating a third example pressure sensor array suitable for use with the present invention.

A diagram illustrating a third example pressure sensor array suitable for use with the present invention is shown in FIG. 9. The pressure sensor array, generally referenced 142, is configured to be in contact with the organ 136 (FIG. 6) when the wearable device 10 (FIG. 1) is properly fastened to the user. In one embodiment, force resistive sensing sheet (i.e. electrically conductive sheet) 168 is mounted on wrist strap 138 and constructed from a piezoresistive material such as Velostat or Linqstat. Pressure sensor array 142 comprises a plurality of sensor elements 164. Each element 164 within the sensor array comprises a set of interdigitated fingers 166 fabricated on either the top or bottom surface of the sensing sheet, a pair of wires 162 connected thereto, a hard material tubular shape cylinder 172 (henceforth referred to as "chimneys" or "meniscus"), and a soft material (e.g., silicone (PDMS), PU) mound 170 dispensed on top of and completely filling chimney 172. When the wrist strap 138 is closed snug around the skin surface 132, the mounds in sensor array 142 touch the skin, and at least one of them will be close to target blood vessel 142. Note that it is preferable that the mounds and cylinders lie substantially over the sensing elements whether they are located on the top or bottom surface of the piezoresistive sheet. The pulse wave from blood vessel 142 travels through its adjacent mounds 170 causing stress to the soft material. Since the volume in chimney 66 is substantially fixed and static, the pressure waveform is transmitted (i.e. channeled) directly to the force resistive sheet 168, and the resistance changes thereof are picked up by conductors 166. The advantage of this configuration is that although the pressure wave is transmitted via a biocompatible soft material (e.g., silicone (PDMS), PU, etc.), that can be worn for extended periods of at least several hours, most of the force is transmitted directly to piezoresistive sheet 168 and to the sensor, and not dispersed in the material causing deformation.

Figure 10:
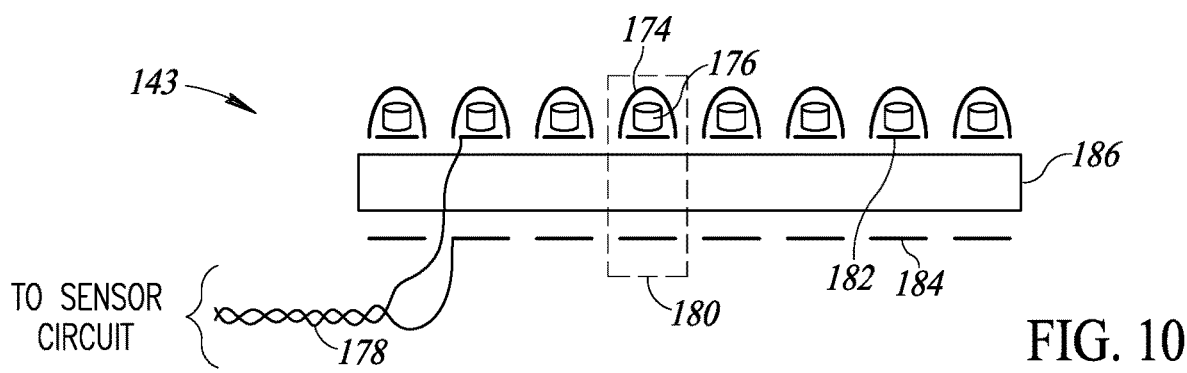
FIG. 10 is a diagram illustrating a fourth example pressure sensor array suitable for use with the present invention.

A diagram illustrating a fourth example pressure sensor array suitable for use with the present invention is shown in FIG. 10. The pressure sensor array, generally referenced 143, is configured to be in contact with the organ 136 (FIG. 6) when the wearable device 10 (FIG. 1) is properly fastened to the user. In one embodiment, force resistive sensing sheet 186 is mounted on wrist strap 138 and constructed from piezoresistive materials such as Velostat or Linqstat. The pressure sensor array 143 comprises a plurality of sensor elements 180. Each element within array 143 comprises a set of opposite conductors 184 and 182, a pair of wires 178 connected thereto, a hard material tubular shape cylinder 176 (henceforth referred to as "chimneys" or "meniscus"), and a soft material (e.g., silicone (PDMS), PU) mound 174 dispensed on top of and completely filling chimney 176. Note that the shape of each conductor is not critical as long as the desired force/resistance relationship is achieved for the particular implementation. Preferably, solid (i.e. contiguous) elements are used on both sides of the sensing sheet. An example of round (button) shaped conductors is shown in FIG. 11B described infra. Note that typically, interdigitated conductive fingers are not used due to the desire to attain as much force dependent resistance from the sensing sheet.

When wrist strap 138 is closed around the skin surface 132, the mounds in array 143 touch the skin and at least one of them will be close to the target blood vessel 133. The pulse wave from blood vessel 133 travels through its adjacent mounds causing stress to the soft material. Since the volume in chimney 176 is constant, the pressure waveform is transmitted directly to the force resistive sheet and its resistance changes are picked up by conductors 182 and 184. The advantage of this method is that although the pressure wave is transmitted via a biocompatible soft material (e.g., silicone (PDMS) or PU), that can be worn for extended periods of at least several hours, most of the force is transmitted directly to piezoresistive sheet 186 and to the sensor, and not dispersed in the material causing deformation.

Figure 11A:
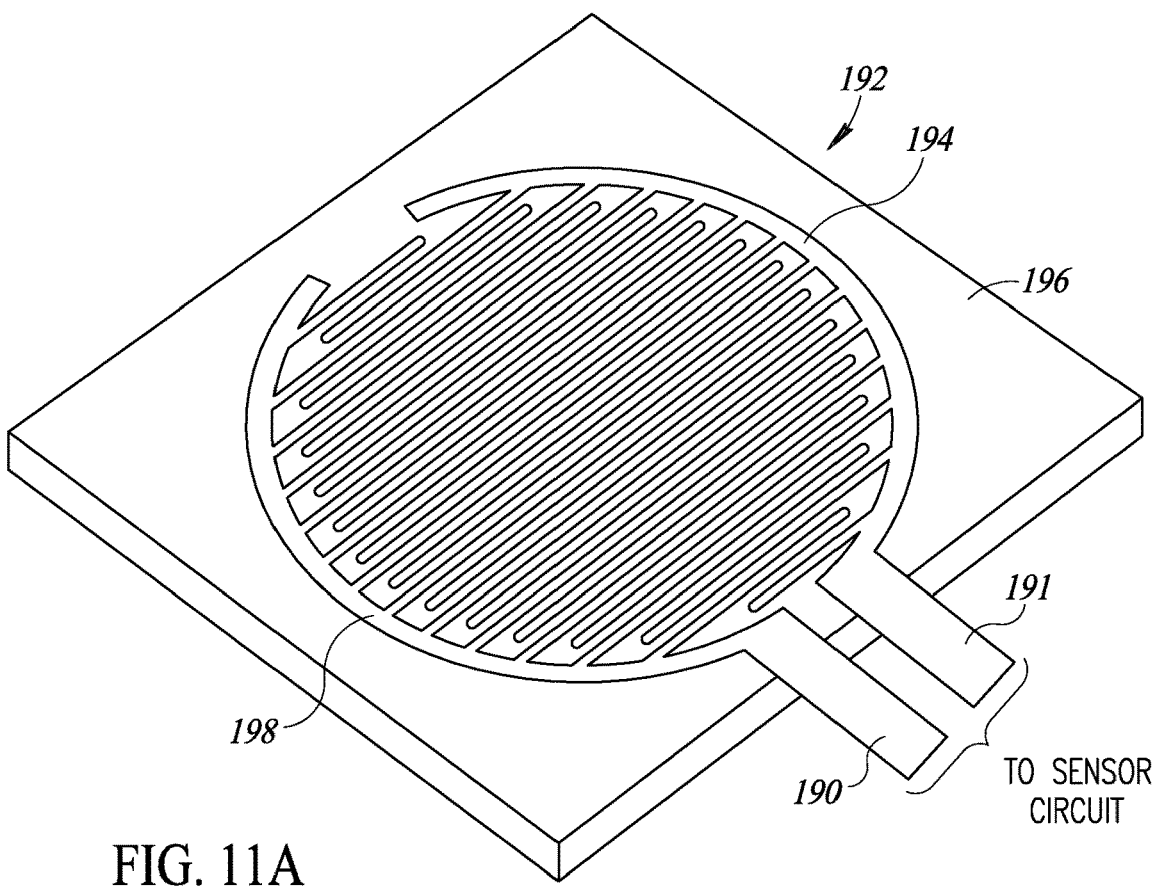
FIG. 11A is a diagram illustrating a first example sensor element in more detail.
Figure 11B:
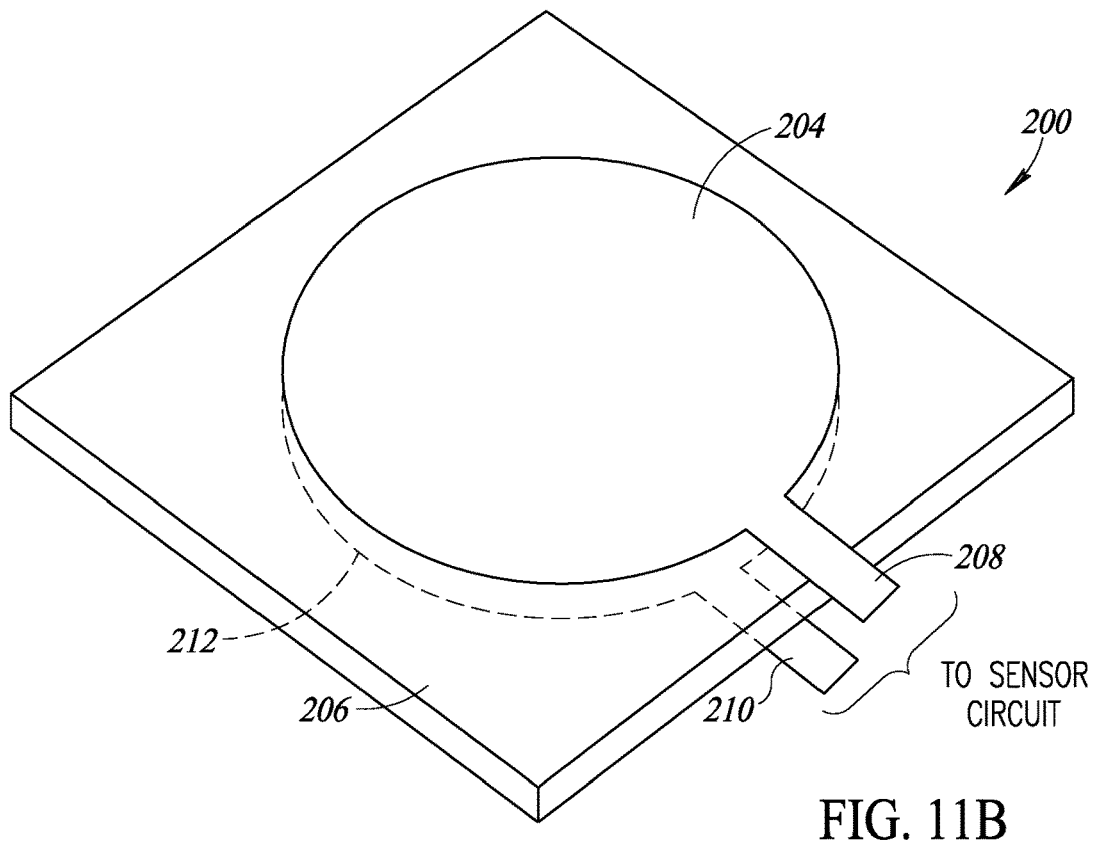
FIG. 11B is a diagram illustrating a second example sensor element in more detail.

A diagram illustrating a first example sensor element in more detail is shown in FIG. 11A. The sensor element, generally referenced 192, is suitable for use as the sensor element in the sensor arrays 140 (FIG. 7) and 142 (FIG. 9). The sensor 192 comprises a force resistive sensing sheet 196 made out of piezoresistive materials such as Velostat or Linqstat, first interdigitated conductive elements 194 printed on one side of the sheet 196 and connected to terminal 191, and second interdigitated conductive elements 198 printed on the same side of the sheet 196 and connected to terminal 190. Both terminals 190 and 191 are coupled to a sensor circuit. It is appreciated that the sensor element is not limited to interdigitated conductive elements but may comprise any suitable pair of conductors spaced apart such that upon the application of pressure the resistance change in the force resistive sensing sheet can be detected by the sensor circuit.

A diagram illustrating a second example sensor element in more detail is shown in FIG. 11B. This second example is suitable for use as the sensor element in the sensor arrays 141 (FIG. 8) and 143 (FIG. 10). In this second example of the sensor element, generally referenced 200, the first conductive element 204 is printed on one side of the force resistive sensing sheet 206 made out of piezoresistive materials such as Velostat or Linqstat and connected to one terminal 208. The second conductive element 212 is printed on the opposite side of the sheet and connected to a second terminal 210. Both terminals 208 and 210 are coupled to a sensor circuit. As described supra, the shape of each conductor is not critical as long as the desired force/resistance relationship is achieved for the particular implementation. Preferably, solid (i.e. contiguous) elements are used on both sides of the sensing sheet.

Figure 12:
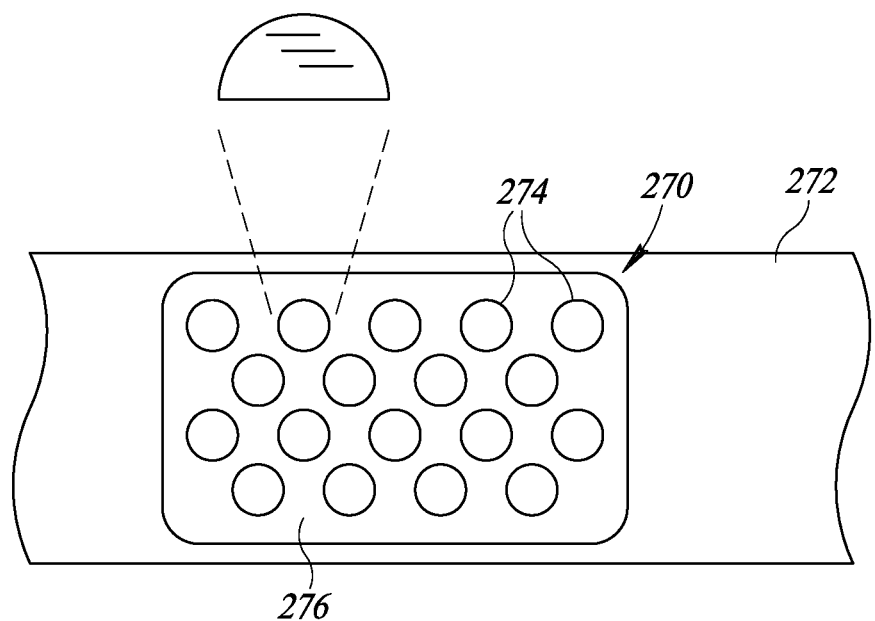
FIG. 12 is a diagram illustrating a top view of an example sensor array of the present invention.

A diagram illustrating a top view of an example sensor array of the present invention is shown in FIG. 12. The array shown is suitable for use in the sensor arrays 140 (FIG. 7) and 141 (FIG. 8). Wrist strap 272 is configured to be closed snug around the skin surface of a tubular extremity organ (e.g., finger, wrist, arm, leg, etc.) containing a target blood vessel (e.g., brachial, radial, ulna, femoral, one of the palmar digital arteries, etc.), while applying moderate pressure. Sensor array 270 comprises a piezoresistive sensor such as Velostat or Linqstat material 276 which is affixed to the wrist strap 272. The sensor array comprises a plurality of protruding mechanical elements 274 affixed to the piezoresistive sheet 276 using any suitable well-known fastening mechanism, e.g., adhesive, glue, etc. As described supra, each protruding mechanical element 274 functions to direct pressure from its top surface in contact with the user to a sensing element coupled to its bottom surface. Each element in the protruding mechanical element array comprises a conductor pair underneath it (not shown) with a pair of wires connected to it. The pair of wires are coupled to a sensor circuit for signal processing.

Figure 13:
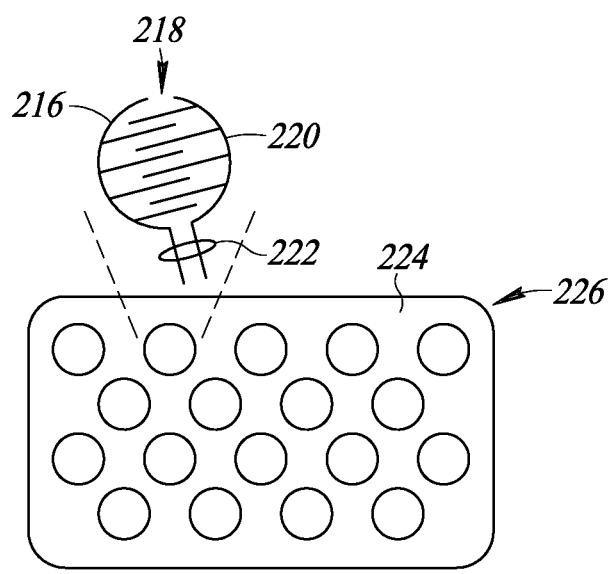
FIG. 13 is a diagram illustrating a bottom view of the example sensor array.

A diagram illustrating a bottom view of the example sensor array is shown in FIG. 13. In this figure, the bottom view of the sensor array 226 including the piezoresistive sheet 224 in accordance with the first embodiment of the present invention is shown. The wrist strap is removed and the bottom of the piezoresistive sheet 224 is visible. For example, sensor elements 140 and 142 of FIGS. 7 and 9, respectively, are shown.

Piezoresistive sheet 224 comprises an array of interdigitated conductive elements 218 affixed to it. Each element comprises two sets of interdigitated fingers 216 and 220. The fingers of each element within the array are fabricated to be close to each other but not to short circuit such that any current flowing through one side must go through piezoresistive sheet 224 in order to reach the other. Interdigitated fingers 216 and 220 are connected to the rest of the system via a set of wires 222. Since the conductivity of the finger sets 216 and 220, as well as the wires 222 is much higher than that of the piezoresistive sheet 224, the resistance measured between wires 222 is dominated by the resistivity of the local area in sheet 224. This allows the detection of a strain wave (i.e. pressure wave) traversing through the area of the sheet encompassed within the finger set 216 and 220 to be detected. In addition, it allows for a reasonably good separation between the various elements, because any area of sheet 224, further away from the immediate vicinity of conductors 216 and 220, will present a much higher resistance with respect to the fingers, than the one adjacent to them.

Figure 14:
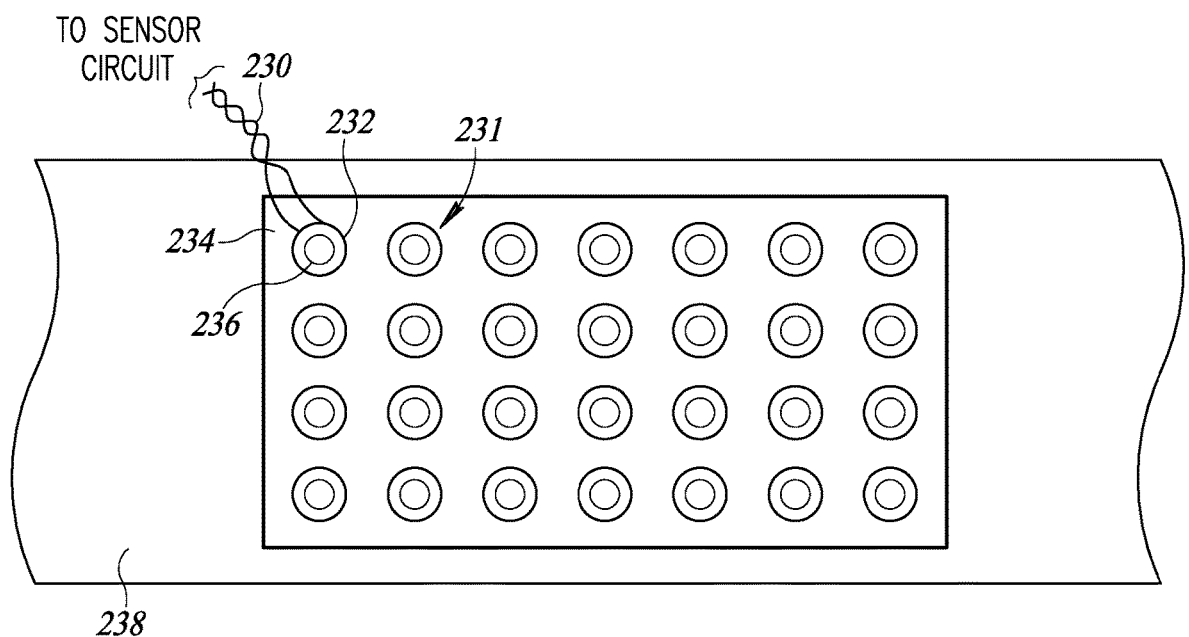
FIG. 14 is a diagram illustrating a top view of another example sensor array of the present invention.

A diagram illustrating a top view of another example sensor array of the present invention is shown in FIG. 14. This sensor array can be used in the arrays 142 and 143 of FIGS. 9 and 10, respectively. Wrist strap 238 is intended to be closed snug around the skin surface of a tubular extremity organ (e.g., finger, wrist, arm, leg, etc.), containing a target blood vessel (e.g., brachial, radial, ulna, femoral, one of the palmar digital arteries, etc.), while applying moderate pressure. A flexible piezoresistive sheet 234 is affixed to the wrist strap 238 and a sensor element array is affixed to sheet 234. Each element 231 in the array contains a pair of wires 230 coming from a pair of conductors (not shown), a tubular shaped element (chimney) 236 made from a hard material (e.g., metal, plastic, etc.), and a mound of soft material 232 dispensed over it. Note that although the sensor array in shown rectangular here, it is appreciated that one skilled in the art may construct sensor arrays having numerous other shapes, such as linear, polygon, diagonal, one dimensional, two dimensional, etc.

Figure 15:
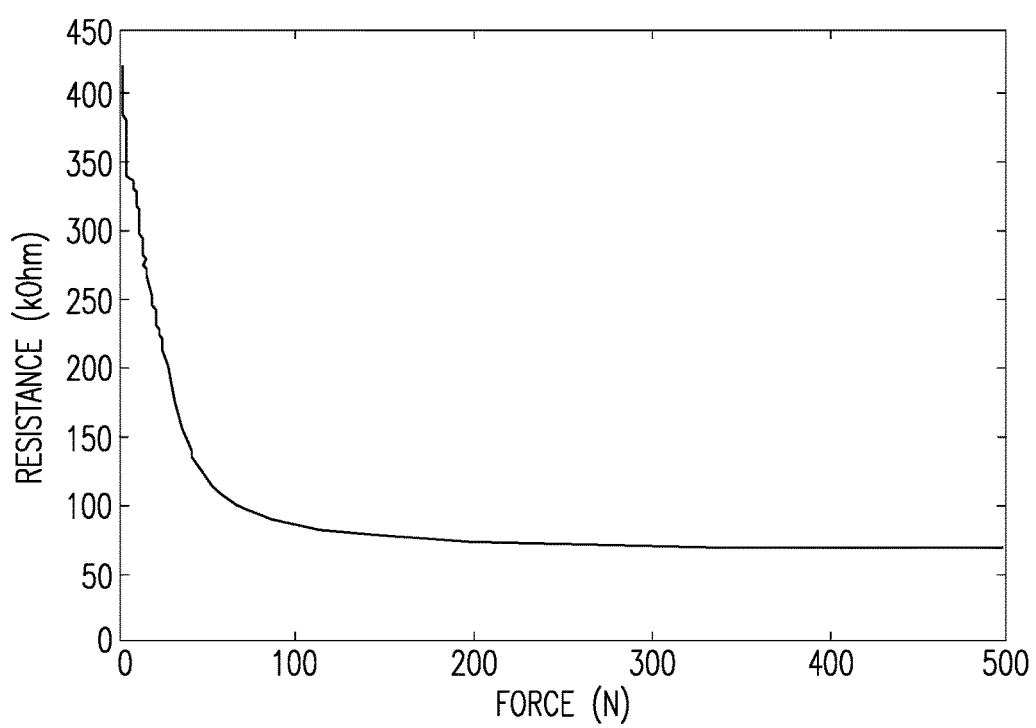
FIG. 15 is a graph illustrating the relationship between resistance and force for the conductive film.

As described supra, the pressure sensor of the present invention utilizes commercially available pressure sensitive material incorporating piezoresistive materials to construct sensors for measuring blood pressure. Piezoresistive materials are those that vary their electrical resistance due to a deformation that is generally caused by an applied force. The relationship between the variation of the electric resistance and the applied force over a piezoresistive material is inversely proportional as shown in FIG. 15. When no force is applied, the electrical resistance of the material is on the order of MOhms and as the applied force increases, the resistance decreases to the range of kOhms or less.

Resistance of piezoresistive materials between electrical contacts is described by the resistance-force relationship shown below.

$$R = \frac{\rho \cdot K}{F} \quad (1)$$

Where $\rho$ is the resistivity of the contacting surfaces, F is the force applied normal to the contact surfaces and K is a function of the roughness and elastic properties of the surfaces.

Figure 16:
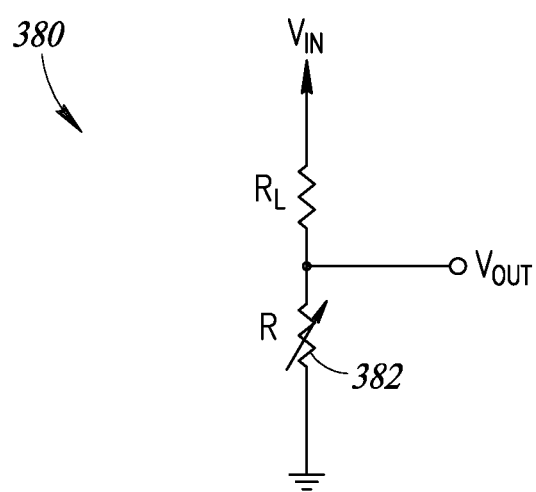
FIG. 16 is a diagram illustrating an example voltage divider circuit for use with the sensor element.

In one embodiment, resistance of the sensor can be converted into a voltage signal utilizing a voltage divider circuit. An example circuit is shown in FIG. 16. The circuit, generally referenced 380, comprises a voltage divider with the sensor R 382 placed in series with a fixed resistor $R_L$. The voltage measured in the sensor-resistor junction is obtained by applying Ohm's law as shown below.

$$V_{OUT} = V_{IN} \cdot \left( \frac{R}{R_L + R} \right) \quad (2)$$

Where $R_L$ is the resistance that completes the voltage divider, $V_{IN}$ is the input voltage applied to the sensor (typically $V_{CC}$), and $V_{OUT}$ is the output of the voltage divider. Voltage-force relationship is given below taking Equations 1 and 2 into account.

$$V_{OUT} = V_{IN} \cdot \left( \frac{\rho \cdot K}{(F \cdot R_L) + (\rho \cdot K)} \right) \quad (3)$$

Note that in one embodiment, a linear response can be obtained by connecting the sensor resistor 382 between a voltage source and an input of a current to voltage converter (i.e. a virtual ground) obtaining a voltage output proportional to the piezoresistive sensor resistance.

Figure 17:
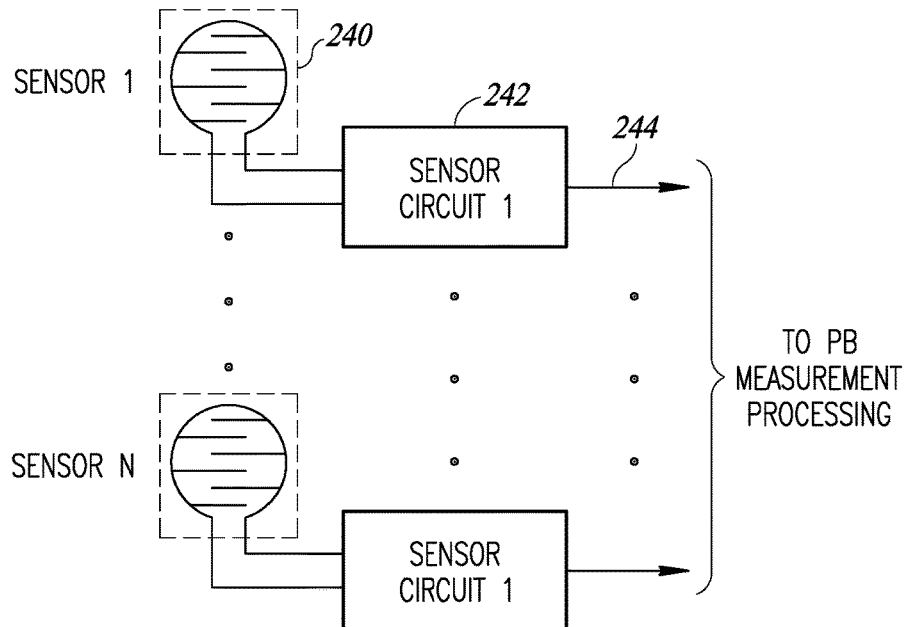
FIG. 17 is a diagram illustrating the connection of a plurality of sensor elements to sensor circuits.

A diagram illustrating the connection of a plurality of sensor elements to sensor circuits is shown in FIG. 17. A plurality of N sensors 240 (N is a positive integer greater than zero) coupled to a corresponding plurality of N sensor circuits 242. The pair of wires from each sensor element is connected to an individual sensor circuit which functions to amplify, and optionally filter the signal from each sensor element. The signal from each sensor is digitized and an output 244 is generated. The N output signals are input to the processor for blood pressure (BP) measurement processing and generation of the blood pressure measurement (systolic and diastolic) that is presented to the user. Note that the sensor elements may comprise any of the sensor elements described supra and may be part of any type of sensor array such as those described supra. Note that depending on the implementation, the signals from the sensor elements may be fed to one or more sensor circuits capable of handling a plurality of signals. Alternatively, each sensor element may have its own corresponding sensor circuit.

Figure 18:
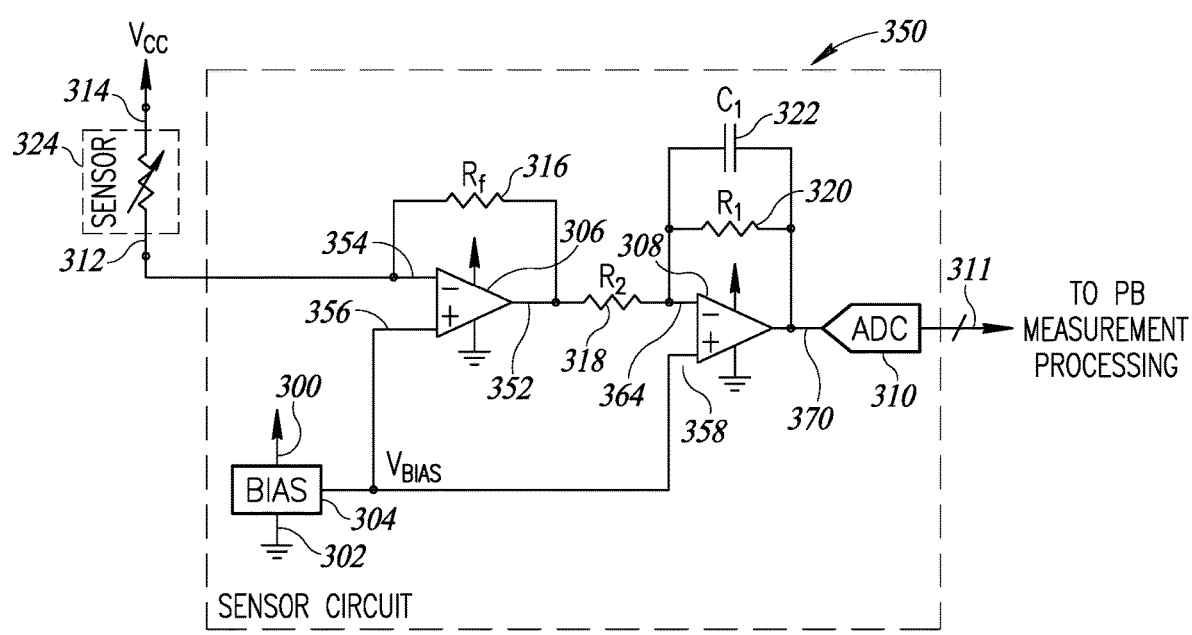
FIG. 18 is a diagram illustrating an example front end circuit coupled to a sensor element.

A diagram illustrating an example front end circuit coupled to a sensor element is shown in FIG. 18. The circuit, generally referenced 350, comprises a supply voltage ($V_{CC}$) 300 from a voltage source and a ground 302 serving as a reference point for the circuit. A bias circuit (e.g., resistive voltage divider, bandgap or a low drop out (LDO) regulator) 304 generates a bias voltage $V_{BIAS}$ 330 between $V_{CC}$ and ground. The bias voltage is connected to the positive inputs 356 and 358 of operational amplifiers 306 and 308, respectively. One terminal 314 of the equivalent resistance 324 of one of the sensor elements printed onto the piezoresistive sheet is connected to $V_{CC}$ and the other terminal 312 is connected to the negative input 354 of operational amplifier 306. The output 352 of operational amplifier 306 is connected via feedback resistor $R_f$ 316 to its negative input 354, thereby creating an inverting transconductance amplifier.

The voltage applied to equivalent resistor 324 is converted into current due to the virtual ground between pins 356 and 354, and due to the high impedance input to operational amplifier 306 is transferred almost completely to feedback resistor $R_f$ 316.

The current multiplied by the value of resistor 316 is the resultant voltage which is subtracted from the bias voltage and present on output pin 352 and the current flowing through resistor 316. Operational amplifier 308 and its adjacent passive components $R_2$ 318, $R_1$ 320 and $C_1$ 322 implement a low pass anti-aliasing filter, converting the voltage at output node 352 into current using resistor $R_2$ 318, and the virtual ground between inputs 358 and 364. This current is almost completely steered into resistor $R_1$ 320 and capacitor $C_1$ 322 connected in parallel between output 370 of operational amplifier 308 and its negative input 364. The output of operational amplifier 308, which provides a low pass filtered voltage biased and proportional to the inverse resistance of equivalent resistor 324 ($1/R_{SENSOR}$), is input to analog to digital converter (ADC) 310, which converts it into a digital sample stream. Note that $1/R_{SENSOR}$ is roughly proportional to the force applied to the piezoresistive sheet.

The digital output signals 311 are input to the processor for subsequent blood pressure measurement processing to generate the blood pressure measurement (systolic and diastolic) that is presented to the user.

Any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermediary components. Likewise, any two components so associated can also be viewed as being "operably connected," or "operably coupled," to each other to achieve the desired functionality.

Furthermore, those skilled in the art will recognize that boundaries between the above described operations merely illustrative. The multiple operations may be combined into a single operation, a single operation may be distributed in additional operations and operations may be executed at least partially overlapping in time. Moreover, alternative embodiments may include multiple instances of a particular operation, and the order of operations may be altered in various other embodiments.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

In the claims, any reference signs placed between parentheses shall not be construed as limiting the claim. The use of introductory phrases such as "at least one" and "one or more" in the claims should not be construed to imply that the introduction of another claim element by the indefinite articles "a" or "an" limits any particular claim containing such introduced claim element to inventions containing only one such element, even when the same claim includes the introductory phrases "one or more" or "at least one" and indefinite articles such as "a" or "an." The same holds true for the use of definite articles. Unless stated otherwise, terms such as "first," "second," etc. are used to arbitrarily distinguish between the elements such terms describe. Thus, these terms are not necessarily intended to indicate temporal or other prioritization of such elements. The mere fact that certain measures are recited in mutually different claims does not indicate that a combination of these measures cannot be used to advantage.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. As numerous modifications and changes will readily occur to those skilled in the art, it is intended that the invention not be limited to the limited number of embodiments described herein. Accordingly, it will be appreciated that all suitable variations, modifications and equivalents may be resorted to, falling within the spirit and scope of the present invention. The embodiments were chosen and described in order to best explain the principles of the invention and the practical application, and to enable others of ordinary skill in the art to understand the invention for various embodiments with various modifications as are suited to the particular use contemplated.

What is claimed is:

1. A sensor array for blood pressure signal acquisition, comprising:
    a substrate having a top surface and a bottom surface, said substrate incorporating a force resistive electrically conductive sensing film; and
    a plurality of sensor elements, each sensor element comprising:
        a mechanical element coupled to said top surface of said sensing film, said mechanical element operative to transfer pressure from its top surface toward said sensing film when in contact with a user, wherein said mechanical element comprises a hard body covered by a soft material; and
        a pair of conductive elements affixed to one of said top or bottom surfaces of said sensing film, said pair of conductive elements spaced apart such that a change in resistance of said sensing film upon application of pressure to said mechanical element is capable of being detected.

2. The sensor according to claim 1, wherein said sensing film comprises a piezoresistive electrically conductive film whose resistance decreases when pressure is applied thereto.

3. The sensor according to claim 1, wherein said hard body and soft cover material are made of materials tailored to have different shore hardness values.

4. The sensor according to claim 1, wherein said mechanical element comprises a relatively hard cylinder and a relatively soft material that covers and/or fills said cylinder, said cylinder operative to guide a pressure wave from a user through said soft material to said sensing film.

5. The sensor according to claim 1, wherein said pair of conductive elements comprises first and second interdigitated conductive elements.

6. The sensor according to claim 5, wherein said first and second interdigitated conductive elements are printed on said bottom surface of said sensing film.

7. The sensor according to claim 1, further comprising a sensor circuit coupled to said pair of conductive elements and operative to generate a digital signal in accordance with a pressure applied to said mechanical element.

8. A sensor array for blood pressure signal acquisition, comprising:
a substrate having a top surface and a bottom surface, said substrate incorporating a force resistive electrically conductive sensing film; and
a plurality of sensing elements, each sensing element comprising:
a first conductive element affixed to said top surface of said sensing film;
a mechanical element coupled to said first conductive element, said mechanical element operative to transfer pressure from its top surface toward said sensing film when in contact with a user, wherein said mechanical element comprises a hard body covered by a soft material; and
a second conductive element affixed to said bottom surface of said sensing film, said first and second conductive elements spaced apart such that a change in resistance of said sensing film upon application of pressure to said mechanical element is capable of being detected.

9. The sensor according to claim 8, wherein said sensing film comprises a piezoresistive electrically conductive film whose resistance decreases when pressure is applied thereto.

10. The sensor according to claim 8, wherein the hard body and soft cover are made of materials tailored to have different shore hardness values.

11. The sensor according to claim 8, wherein said mechanical element comprises a relatively hard cylinder and a relatively soft material that covers and/or fills said cylinder, said cylinder operative to guide a pressure wave from a user through said soft material to said sensing film.

12. The sensor according to claim 8, wherein said first and second conductive elements comprise first and second digitated conductive elements.

13. The sensor according to claim 12, wherein said first and second digitated conductive elements are printed on said top and bottom surfaces, respectively, of said sensing film.

14. The sensor according to claim 8, further comprising a sensor circuit coupled to said first and second conductive elements and operative to generate a digital signal in accordance with a pressure applied to said mechanical element.

15. A wearable device for measuring blood pressure of a user, comprising:
a housing;
a display mounted in said housing;
a wrist strap coupled to said housing;
a processor coupled to a memory;
at least one sensor array including a plurality of sensing elements coupled to a sensor circuit and operative to acquire a blood pressure signal;
each sensing element comprising:
a substrate having a top surface and a bottom surface, said substrate incorporating a force resistive electrically conductive sensing film;
a mechanical element coupled to said top surface of said sensing film, said mechanical element operative to transfer pressure from its top surface toward said sensing film when in contact with a user, wherein said mechanical element comprises a hard body covered by a soft material; and
first and second conductive elements affixed to said sensing film, said first and second conductive elements spaced apart such that a change in resistance of said sensing film upon application of pressure to said mechanical element is capable of being detected.

16. The sensor according to claim 15, wherein said mechanical element comprises a relatively hard cylinder and a relatively soft material that covers and/or fills said cylinder, said cylinder operative to guide a pressure wave from a user through said soft material to said sensing film.

17. The sensor according to claim 15, wherein said first conductive element is printed on said top surface of said sensing film and said second conductive element is printed on said bottom surface of said sensing film.

18. The sensor according to claim 15, wherein both said first and second conductive elements are printed on one of said top or bottom surfaces of said sensing film as a pair of interdigitated fingers.

* * * * *